United States Patent
Sutherland et al.

(10) Patent No.: US 7,297,795 B2
(45) Date of Patent: Nov. 20, 2007

(54) PROCESS FOR PREPARATION OF 4-AMINO-3-QUINOLINECARBONITRILES

(75) Inventors: Karen Wiggins Sutherland, New City, NY (US); Gregg Brian Feigelson, Chester, NY (US); Diane Harris Boschelli, New City, NY (US); David Michael Blum, Upper Saddle River, NJ (US); Henry Lee Strong, Somerset, NJ (US)

(73) Assignee: Wyeth Holdings Corporation, Madison, NJ (US)

( * ) Notice: Subject to any disclaimer, the term of this patent is extended or adjusted under 35 U.S.C. 154(b) by 383 days.

(21) Appl. No.: 10/918,947

(22) Filed: Aug. 16, 2004

(65) Prior Publication Data

US 2005/0043537 A1 Feb. 24, 2005

Related U.S. Application Data

(60) Provisional application No. 60/496,191, filed on Aug. 19, 2003.

(51) Int. Cl.
C07D 215/44 (2006.01)

(52) U.S. Cl. .................................. 546/159; 546/160

(58) Field of Classification Search ............... 546/159, 546/160
See application file for complete search history.

(56) References Cited

OTHER PUBLICATIONS

Chem. Abstracts 71:70269, Abstract of Kolmiets et al, Zhumal Prikladnou Khimii (Sankt-Peterburg, Russian Federation, vol. 42 (4), p. 963-966 (1969).*
Meth-Cohn, O.; et al.; The Reverse Vilsmeier Approach to the Synthesis of Quinolines, Quinolinium Salts and Quinolones; Tetrahedron 51:47:12869-12882, 1995.
Price, C.C.; et al.; A Synthesis of Substituted 4-Aminoquinolines; J. Am. Chem. Soc. 68:1246-1250, 1946.
Snyder, H.R.; et al.; Synthesis of 4-Hydroxyquinolines. III. A Direct Synthesis of β-Substituted Acrylic Esters; J. Am. Chem. Soc. 68:1253-1255, 1946.
Marsilje, T.H.; et al.; The Design, Synthesis and Activity of Non-ATP Competitive Inhibitors of pp60[c-src] Tyrosine Kinase. Part 1: Hydroxynaphthalene Derivatives; Bioorg. Med. Chem. Lett. 10:477-481, 2000.
Wolfbeis, O.S.; Zur Darstellung von Aminomethylenderivaten offenkettiger $CH_2$-acider Verbindungen; Chem. Ber. 114:3471-3484, 1981.
Lunt, E.; et al.; Antitumor Imidazotetrazines. 14. Synthesis and Antitumor Activity of 6- and 8- Substituted Imidazo[5,1-d]-1,2,3,5-tetrazinones and 8-Substituted Pyrazolo[5,1-d]-1,2,3,5-tetrazinones; J. Med. Chem. 30:357-366, 1987.
Kuo, E.A.; et al.; Synthesis, Structure-Activity Relationships, and Pharmacokinetic Properties of Dihydroorotate Dehydrogenase Inhibitors: 2-Cyano-3-cyclopropyl-3-hydroxy-N-[3'-methyl-4'-(trifluoromethyl)phenyl]propenamide and Related Compounds; J. Med. Chem. 39:4608-4621, 1996.
Sjogren, E.B.; et al.; Synthesis and Biological Activity of a Series of Diaryl-Substituted α-Cyano-β-hydroxypropenamides, a New Class of Anthelmintic Agents; J. Med. Chem. 34:3295-3301, 1991.
March, Jerry; Advanced Organic Chemistry, Reactions, Mechanisms, and Structure, 3rd Edition; 1985, John Wiley & Sons, New York, pp. 371-373; Paragraph 0-56.

* cited by examiner

Primary Examiner—Bernard Dentz
(74) Attorney, Agent, or Firm—Stephen E. Johnson

(57) ABSTRACT

This invention discloses a process for the preparation of a 4-amino-3-quinolinecarbonitrile comprising combining an amine compound with a cyanoacetic acid and an acid catalyst to yield a cyanoacetamide; condensing the cyanoacetamide with an optionally up to tetra-substituted aniline in an alcoholic solvent and a trialkylorthoformate to yield a 3-amino-2-cyanoacrylamide; combining the 3-amino-2-cyanoacrylamide with phosphorus oxychloride in acetonitrile, butyronitrile, toluene or xylene, optionally in the presence of a catalyst to yield a 4-amino-3-quinolinecarbonitrile and also discloses a process for the preparation of a 7-amino-thieno[3,2-b]pyridine-6-carbonitrile comprising combining a disubstituted 3-amino thiophene with a cyanoacetamide and trialkylorthoformate in an alcoholic solvent to obtain a 3-amino-2-cyanoacrylamide; and combining the 3-amino-2-cyanoacrylamide with phosphorus oxychloride and acetonitrile, butyronitrile, toluene or xylene, optionally in the presence of a catalyst to yield a 7-amino-thieno[3,2-b]pyridine-6-carbonitrile and also discloses a process for the preparation of a 4-amino-3-quinolinecarbonitrile by combining an amine compound with a cyanoacetic acid and a peptide coupling reagent to obtain a suspension; filtering the suspension to yield a cyanoacetamide; condensing the cyanoacetamide with an optionally up to tetra-substituted aniline, an alcoholic solvent, and triethylorthoformate to yield a 3-amino-2-cyanoacrylamide; and combining the 3-amino-2-cyanoacrylamide with phosphorus oxychloride to yield a 4-amino-3-quinolinecarbonitrile.

13 Claims, No Drawings

PROCESS FOR PREPARATION OF 4-AMINO-3-QUINOLINECARBONITRILES

This application claims priority from copending provisional application Ser. No. 60/496,191, filed Aug. 19, 2003, the entire disclosure of which is hereby incorporated by reference.

BACKGROUND OF THE INVENTION

This invention relates to the manufacture of 4-amino-3-quinolinecarbonitriles, which can serve as intermediates for the synthesis of additional 4-amino-3-quinolinecarbonitrile analogues. Such substituted quinolines, as well as the pharmaceutically acceptable salts thereof, inhibit the action of certain protein kinases (PK) thereby inhibiting the abnormal growth of certain cell types.

The compounds derived from this invention are for example, useful in the treatment of polycystic kidney disease, colonic polyps, cancer, and stroke in mammals.

Throughout this patent application the quinoline ring system will be numbered as indicated in the formula below:

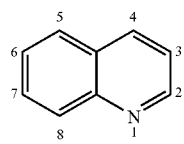

This invention also relates to the manufacture of 7-amino-thieno[3,2-b]pyridine-6-carbonitriles useful as intermediates in the synthesis of 7-amino-thieno[3,2-b]pyridine-6-carbonitrile analogues. Throughout this patent application the thieno[3,2-b]pyridine ring system will be numbered as indicated in the formula below:

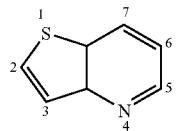

Historically there are several methods for the preparation of 4-aminosubstituted quinolines and the two most frequent methods involve intramolecular Friedel-Crafts reactions or electrocyclic ring closures of N-(2-carboxyvinyl)-aniline derivatives at elevated temperatures. Cyclodehydration of suitable amide substrates via Vilsmeier type intermediates appears attractive but the literature is scarce and in the example below, the desired amino-quinoline species is unstable under the reaction conditions and the chloro-quinoline is favored [Meth-Cohn, O., Taylor, D. L. (1995) *Tetrahedron*, 51, 12869].

The approach described herein is favorable due to the relative ease of preparation of the cyanoacetamide portion from cyanoacetic acid and the desired aniline and suitably substituted aniline that results in the carbocyclic ring. One example exists in the literature where 3-chloroaniline is reacted via a variety of cyanoacetamides to form enaminonitriles, which undergo cyclization to 4-aminoquinolines in some cases. The conditions used to prepare the enaminonitrile are much harsher than those outlined herein and cyclization conditions in some examples do not result in cyclodehydration [Price, C. C., Boekelheide, V. (1946) J. Am. Chem. Soc., 68, 1246]. In addition, the compounds described in this invention contain significantly different substitution patterns.

BRIEF SUMMARY OF THE INVENTION

The present invention relates to a process for the preparation of a 4-amino-3-quinolinecarbonitrile comprising combining an amine compound with cyanoacetic acid and an acid catalyst to yield a cyanoacetamide; condensing the cyanoacetamide with an optionally up to tetra-substituted aniline in an alcoholic solvent and a trialkylorthoformate to yield a 3-amino-2-cyanoacrylamide, and then combining the 3-amino-2-cyanoacrylamide with phosphorus oxychloride in acetonitrile, butyronitrile, toluene or xylene, optionally in the presence of a catalyst to yield a 4-amino-3-quinolinecarbonitrile.

The present invention also relates to a process for the preparation of a 7-amino-thieno[3,2-b]pyridine-6-carbonitrile comprising combining an optionally up to disubstituted 3-amino thiophene with a cyanoacetamide and trialkylorthoformate in an alcoholic solvent to obtain a 3-amino-2-cyanoacrylamide and combining the 3-amino-2-cyanoacrylamide with phosphorus oxychloride in acetonitrile, butyronitrile, toluene or xylene, optionally in the presence of a catalyst to yield a 7-amino-thieno[3,2-b]pyridine-6-carbonitrile.

In addition, the present invention relates to a process for the preparation of a 4 amino-3-quinolinecarbonitrile by combining an amine compound with cyanoacetic acid and a peptide coupling reagent to obtain a solution, filtering the solution to yield a cyanoacetamide; condensing the cyanoacetamide with an optionally up to tetra-substituted aniline, an alcoholic solvent, and a trialkylorthoformate to yield a 3-amino-2-cyanoacrylamide; and combining the 3-amino-2-cyanoacrylamide with phosphorus oxychloride to yield a 4-amino-3-quinolinecarbonitrile.

The present invention includes a process for the preparation of a cyanoacetamide comprising combining dimethylformamide (DMF), an amine and cyanoacetic acid to yield a mixture; cooling the mixture; adding a solution of N,N' dicyclohexylcarbodiimide in DMF so as to keep the temperature below 15° C. to yield a suspension; filtering the suspension and washing the resulting solid by-product to yield a filtrate; adding water to the filtrate to obtain a mixture; and filtering the mixture to yield a cyanoacetamide The following experimental details are set forth to aid in an understanding of the invention, and are not intended, and should not be construed, to limit in any way the invention set forth in the claims that follow thereafter.

DETAILED DESCRIPTION OF THE INVENTION

This invention provides a high yielding, high purity, operationally simple process for the production of 4-amino-3-quinolinecarbonitriles optionally with substituents in 5, 6, 7, and 8 positions, comprising:
  (a) preparation of a cyanoacetamide;
  (b) preparation of a 3-amino-2-cyanoacrylamide of optionally substituted anilines using a cyanoacetamide and a trialkylorthoformate; and
  (c) cyclodehydration of the 3-amino-2-cyanoacrylamide prepared as above with phosphorus oxychloride in a suitable solvent with or without additional tertiary amine bases or alcohols.

The methodology described herein constructs a functionalized aniline, containing substituents that permit intramolecular cyclization under dehydrating conditions.

The sequence illustrated below describes the invention claimed herein.

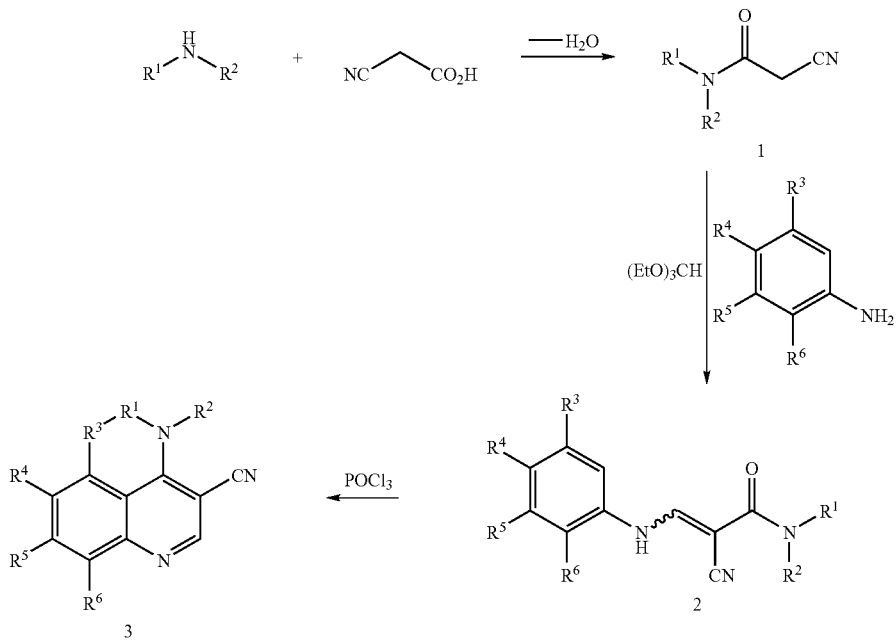

wherein:

$R^1$ and $R^2$ are each independently hydrogen, alkyl of 1-6 carbon atoms, substituted and unsubstituted aryl; and $R^3$, $R^4$, $R^5$ and $R^6$ are each independently hydrogen, hydroxy, halogen, alkyl of 1-6 carbon atoms, alkenyl of 2-6 carbon atoms, alkynyl of 2-6 carbon atoms, alkoxy of 1-6 carbon atoms, -alkoxyalkoxy-, haloalkoxy-, -alkylheteroaryl, optionally substituted aryl, N-alkylpiperazino wherein the alkyl moiety is of 1-6 carbon atoms, pyrrolidino, morpholino, piperazino, -alkoxy[(N)-alkylpiperazino] wherein the alkyl and alkoxy moiety are of 1-6 carbon atoms, or optionally substituted heteroaryl.

The cyanoacetamide 1 can be prepared from the corresponding amine and cyanoacetic acid in refluxing toluene with an acid catalyst or in tetrahydrofuran (THF) with a peptide coupling reagent. The examples contained herein provide preferred conditions and include use of 1.03 equivalents of cyanoacetic acid relative to amine and 1,3-diisopropylcarbodiimide in THF at 77-80° C. The optimum procedure allows for filtration of the suspension then dilution with water to allow the product to precipitate and collecting by filtration. This procedure provides a near quantitative yield 1 of sufficient purity to be used in the subsequent step without further purification.

Use of a water-soluble peptide coupling reagent in THF permits direct isolation of the cyanoacetamide on treatment with water.

The condensation reaction of the cyanoacetamide with optionally up to tetra-substituted anilines can be performed with the hydrochloride salt or free base of the aniline with trialkylorthoformate using alcoholic solvents at 20-140° C. The optimum conditions for this transformation result from conducting the reaction in iso-propanol at 80° C. with the hydrochloride salt or free base of the aniline and 2.0-7.0 equivalents of triethylorthoformate. These conditions allow for precipitation of the product 2 that is isolated after filtration in good yield and high purity and can be used in the subsequent step without purification.

The cyclo-dehydration is accomplished with phosphorus oxychloride in acetonitrile, butyronitrile, toluene or xylene optionally with alcohols or amine bases as catalysts at 80-110° C. The transformation may be done by heating the substrate in acetonitrile or butyronitrile with methanol and phosphorus oxychloride. The product salt precipitates from the reaction and can be neutralized directly or isolated and neutralized in a separate vessel to produce 3 in good yield and high quality. Addition of base to the reaction, such as pyridine, triethylamine, or diisopropylamine can provide a significant rate acceleration.

In accordance with this invention a high yielding and operationally simple process for the production 7-amino-thieno[3,2-b]pyridine-6-carbonitriles in high purity is provided by a process, which comprises the sequence illustrated below:

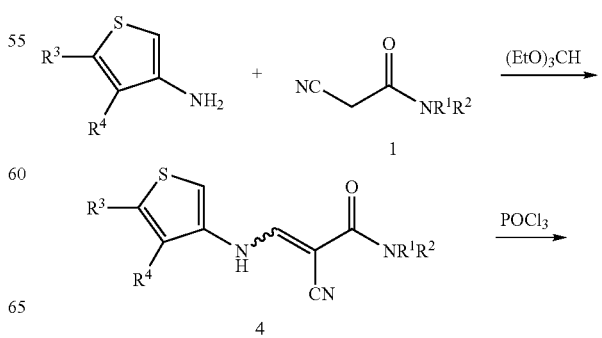

-continued

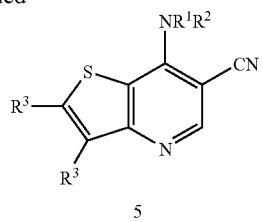

wherein:

R[1] and R[2] are each independently hydrogen, alkyl of 1-6 carbon atoms substituted and unsubstituted aryl; and R[3] and R[4] are each independently hydrogen, halogen, alkyl of 1-6 carbon atoms, alkenyl of 2-6 carbon atoms, alkynyl of 2-6 carbon atoms, -alkylheteroaryl, aryl, or heteroaryl.

The condensation reaction of the cyanoacetamide 1 with 3-aminothiophene can be performed with the hydrochloride salt or free base of 3-aminothiophene with trialkylorthoformate using alcoholic solvents at 20-140° C. The optimum conditions for this transformation result from conducting the reaction in iso-propanol at 80° C. with 3-aminothiophene and 2.0-7.0 equivalents of triethylorthoformate. These conditions allow for precipitation of the product 4 isolated after filtration in good yield and high purity and can be used in the subsequent step without purification.

The cyclo-dehydration is accomplished with phosphorus oxychloride in acetonitrile, butyronitrile, toluene or xylene optionally with alcohols or amine bases as catalyst at 80-110° C. The optimum procedure for this transformation is by heating the substrate in acetonitrile with phosphorus oxychloride. The product salt precipitates from the reaction and can be neutralized directly or isolated and neutralized in a separate vessel to produce 7-amino-thieno[3,2-b]pyridine-6-carbonitriles of formula 5 in good yield and high quality.

The described route 1 is shown using the following examples 4, 6, 42, 43, 44 and 45.

The described route 2 is shown using the following examples 4, 46, 47, 48, 49, and 50.

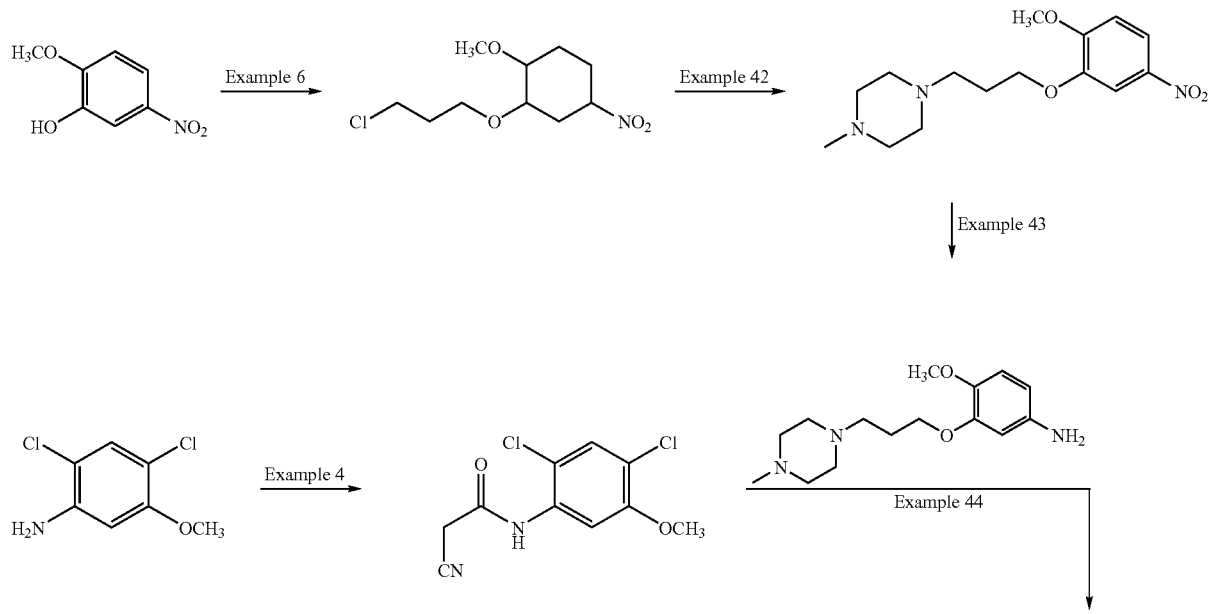

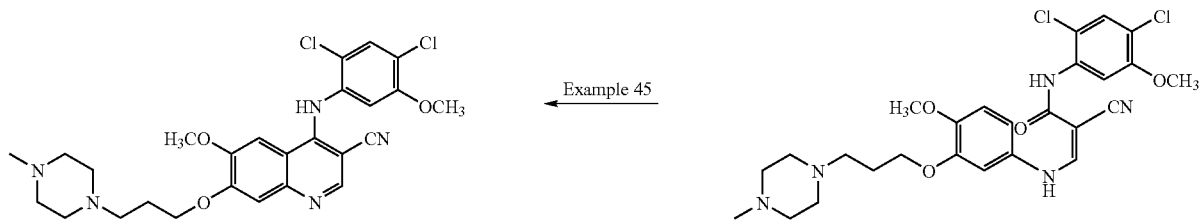

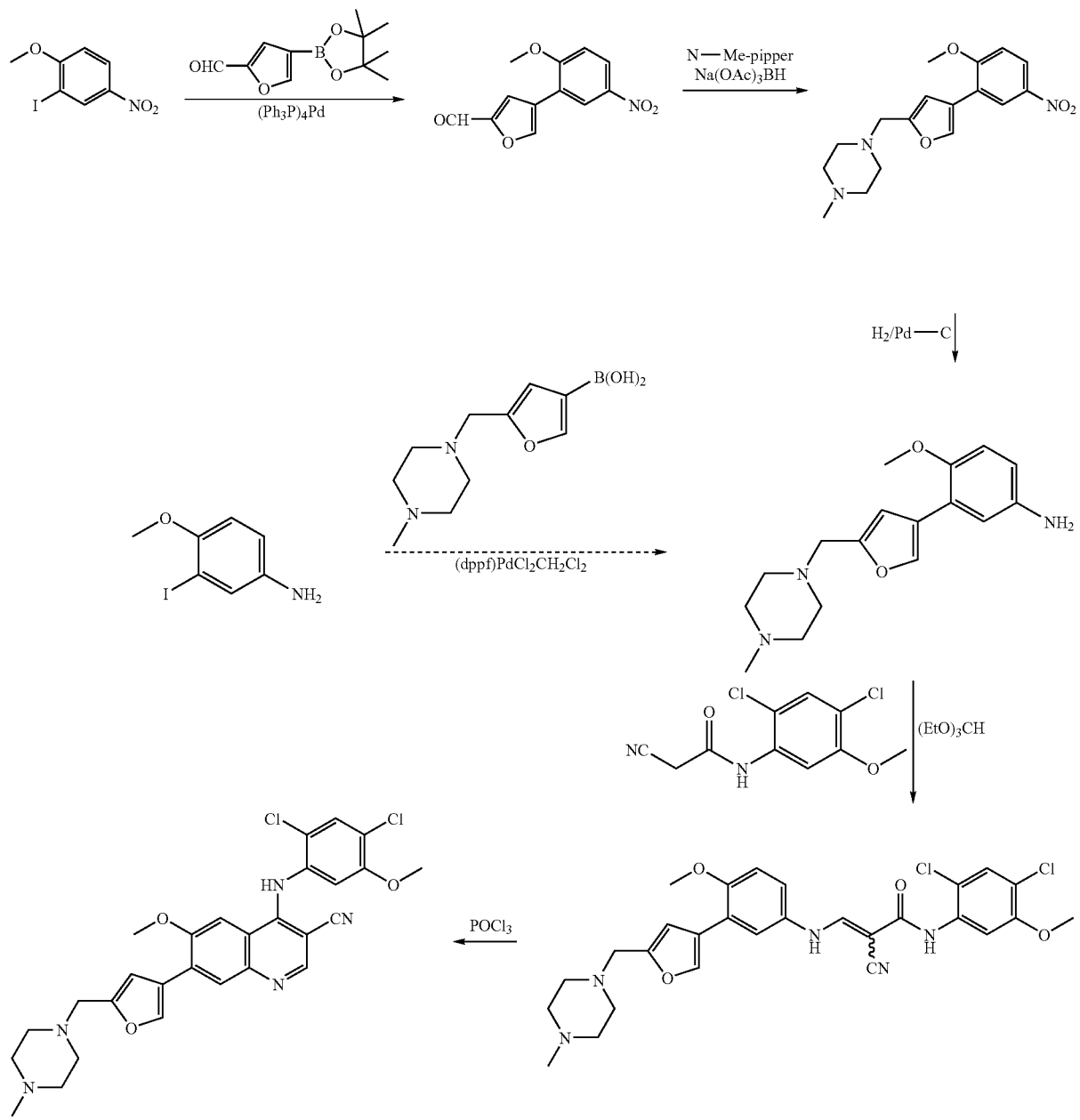

In certain embodiments of the invention the cyanoacetic acid is used in an amount of 1-1.5 equivalents relative to the amine, with a preferred concentration of 1.03 equivalents.

In certain embodiments of the invention the optionally up to tetra-substituted aniline is a hydrochloride salt. In another embodiment the optionally up to tetra-substituted aniline is a free base.

DEFINITIONS

For convenience, certain terms employed in the specification, examples, and appended claims are collected here.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In a preferred embodiment , a straight chain or branched chain alkyl has 6 or fewer carbon atoms in its backbone. The term "alkyl" can be used alone or as part of a chemical name as in for example, "trialkylorthoformate".

The terms "alkenyl" and "alkynyl" refer to unsaturated aliphatic groups analogous in length and possible substitution to the alkyls described above, but which contain at least one double or triple carbon-carbon bond, respectively.

The term "alkoxy" as used herein refers to an alkyl group, as defined above, having an oxygen radical attached thereto. Representative alkoxyl groups include methoxy, ethoxy, propyloxy, tert-butoxy and the like. The term alkoxy can be used alone or as part of a chemical name as in for example, "alkoxy-enaminonitrile".

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6-, 7- and 10-membered carbocyclic single ring or fused multiple ring aromatic groups, which may be substituted or unsubstituted.

The term "heteroaryl" refers to a 4 to 10 aromatic membered ring structure, which ring structure includes one to four heteroatoms. Heteroaryls include, but are not limited to, pyrrolidine, oxolane, thiolane, piperidine, piperazine, pyrrole, furan, thiophene, imidazole, oxazole, thiazole, triazole, pyrazole, pyridine, pyrazine, pyridazine and pyrimidine, and morpholine.

The term "heteroatom" as used herein means an atom of any element other than carbon or hydrogen. Preferred heteroatoms are nitrogen, oxygen, sulfur, phosphorus, and selenium.

The term "halogen" refers to an atom of fluorine, chlorine, bromine, or iodine.

As used herein, the term "substituted" is contemplated to include all permissible substituents of organic compounds. In a broad aspect, the permissible substituents of organic compounds include acyclic and cyclic, branched and unbranched, carbocyclic and heterocyclic, aromatic and nonaromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

As used herein the acid and base catalysts of this invention include a substance that increases the rate of a reaction without modifying the overall standard Gibbs energy change in the reaction. In a preferred embodiment the acid and base catalysts include for example, pyridine and 3-nitrophenylboronic acid.

As used herein the peptide coupling reagent includes for example, 1,3-diisopropylcarbodiimide, 1,3-[(dimethylamino)propyl]-3-ethylcarbodiimide hydrochloride, and dicyclohexylcarbodiimide (DCC).

As used herein the alcoholic solvent is the liquid or homogeneous mixture of liquids in which extractant(s) and possible modifier(s) may be dissolved to form the solvent phase. In an embodiment the alcoholic solvent is for example ethylene glycol, methanol, iso-propanol, or butanol. In a preferred embodiment the alcoholic solvent is iso-propanol.

As used herein the condensing step of the present invention occurs at a temperature of 10-200° C. In a more preferred embodiment the temperature is 140° C. In another preferred embodiment the temperature is 80° C.

In a certain embodiment of this invention the catalyst is an alcohol. In another embodiment the catalyst is an amine base.

In an embodiment of the invention the peptide coupling reagent is water soluble.

EXAMPLE 1

(3-Chloro-4-fluorophenyl)-2-cyanoacetamide

A 5-L round-bottomed flask under $N_2$ equipped with an overhead stirrer, a condenser, thermocouple and 500 mL dropping funnel was charged with cyanoacetic acid (150 g, 1.77 mol), 3-chloro-4-fluoroaniline (250 g, 1.72 mol) and tetrahydrofuran (THF) (750 mL). The mixture was heated to 75° C. A solution of 1,3-diisopropylcarbodiimide (221.6 g, 275 mL, 1.77 mol) in THF (50 mL) was added dropwise over 25 minutes at 75-79° C. At the end of the addition diisopropylurea precipitated from solution. The suspension was stirred for an hour then cooled to 13° C. The suspension was filtered and the filter cake washed with THF (2×250 mL). The filtrate was transferred to a 2 L dropping funnel and the solids discarded.

A 12-L round-bottomed flask equipped with overhead stirrer and thermocouple was charged with water (4250 mL) at 15° C. The filtrate from above was added slowly to the water over 25 minutes forming a white suspension. The suspension was stirred at room temperature overnight.

The suspension was filtered and the filter cake washed with water (2×250 mL) and dried under vacuum (50 mm Hg) at 45° C. to provide (3-chloro-4-fluorophenyl)-2-cyanoacetamide as a white solid (294.5 g, 81% yield, >99% purity by HPLC, mp 155.7-157° C.). $^1$H NMR (300 MHz, DMSO-$d_6$): 10.4 (s, 1H), 7.80 (d, J=8 Hz, 1H), 7.5-7.3 (m, 2H), 3.92 (s, 2H).

EXAMPLE 2

(3-Chloro-4-fluorophenyl)-2-cyanoacetamide

A 500-mL round bottomed flask under $N_2$ equipped with overhead stirrer, a condenser, thermocouple and 100 mL dropping funnel was charged with 1-[3-(dimethylamino)propyl]-3-ethylcarbodiimide hydrochloride (21.17 g, 0.11 ml) and THF (140 mL). A solution of cyanoacetic acid (10.03 g, 0.118 mol) and 3-chloro-4-fluoroaniline (15.44 g, 0.106 mol) in THF (60 mL) was added to the dropping funnel and added to the reaction flask at 25-45° C. At the end of the addition the reaction became a clear solution. The solution was stirred at ambient temperature for 1.5 hours then poured slowly into water (500 mL) forming a white suspension. The suspension was stirred at room temperature overnight then filtered and the filter cake washed with water and dried under vacuum (50 mm Hg) at 45° C. to provide (3-chloro-4-fluorophenyl)-2-cyanoacetamide as a white solid (21.27 g, 94% yield, 97.5% by HPLC). $^1$H NMR (300 MHz, DMSO-$d_6$): 10.4 (s, 1H), 7.80 (d, J=8 Hz, 1H), 7.5-7.3 (m, 2H), 3.92 (s, 2H).

EXAMPLE 3

(3-Chloro-4-fluorophenyl)-2-cyanoacetamide

A 500-mL round bottomed flask under $N_2$ equipped with overhead stirrer, a Dean-Stark trap and condenser, thermocouple was charged with cyanoacetic acid (28.04 g, 0.33 mol), 3-chloro-4-fluoroaniline (40.0 g, 0.28 mol), 3-nitrophenylboronic acid (2.28 g, 0.014 mol) and toluene (200 mL). The mixture was heated to reflux and water collected in the Dean-Stark trap. After 5.5 hours, thin layer chromatography (TLC) indicated complete consumption of the aniline. The reaction mixture was cooled to room temperature (RT) forming a pink suspension. The solids were isolated by filtration, washed with MTBE (2×200 mL) and dried to afford (3-chloro-4-fluorophenyl)-2-cyanoacetamide as a pale pink solid (46.40 g, 79% yield, 96.7% by GC-MS). $^1$H NMR (300 MHz, DMSO-$d_6$): 10.4 (s, 1H), 7.80 (d, J=8 Hz, 1H), 7.5-7.3 (m, 2H), 3.92 (s, 2H).

EXAMPLE 4

2-Cyano-N-(2,4-dichloro-5-methoxyphenyl)acetamide 2,4-Dichloro-5-methoxyaniline (5.00 g, 26 mmol) and cyanoacetic acid (2.28 g, 26.8 mmol) were mixed in 50 mL of tetrahydrofuran until a solution formed. This solution was heated to reflux and 1,3-diisopropylcarbodiimide (4.2 mL, 26.8 mmol) was added dropwise. After 30 minutes the mixture was cooled to ~15° C. in an ice-bath. The solid was collected by filtration and washed with tetrahydrofuran. The filtrate was slowly poured into water and stirred for 30 minutes. The white solid was collected by filtration, washed with water, and was then dissolved in 500 mL of ethyl acetate. The solution was dried over sodium sulfate and concentrated in vacuo to give 5.9 g (88%) of 2-cyano-N-(2,4-dichloro-5-methoxyphenyl)acetamide as a white solid, mp 180-181° C.; $^1$H NMR (400 MHz, DMSO-$d_6$) δ 3.84 (s, 3H), 4.02 (s, 2H), 7.58 (s, 1 H), 7.66 (s, 1 H), 10.00 (s, 1 H); MS (ES) m/z257.0, 259.0 (M−H)−

Analysis for $C_{10}H_8Cl_2N_2O_2$; Calcd: C, 46.36; H, 3.11; N, 10.81. Found: C, 46.25; H, 3.10; N, 10.85.

ALTERNATIVE EXAMPLE 4

A reaction flask was charged with dimethylformamide (DMF) (500 mL), 2,4-dichloro-5-methoxyaniline (100 g, 0.52 mol) and cyanoacetic acid (46.6 g, 0.55 mol). The mixture was cooled to 10° C. in an ice bath. To the cooled mixture was added, dropwise, a solution of N,N' dicyclohexylcarbodiimide (119.1 g, 0.58 mol) in DMF (240 mL) so as to keep the temperature below 15° C. After the addition was completed, cooling was discontinued and the reaction was stirred for 2 hours. The urea by-product was then removed via filtration and the cake was washed twice with DMF. To the filtrate was added 700 mL of water. The solid product emerged from solution. The slurry was cooled to 5° C. and held for at least 30 minutes. The product was collected by filtration and washed with water and then dried in vacuo at 60° C. to give 127.08 g of light tan solid.

EXAMPLE 5

2-Cyano-N-(3,4,5-trimethoxyphenyl)acetamide 3,4,5-Trimethoxyaniline (10.00 g, 54.6 mmol) and cyanoacetic acid (4.78 g, 56.19 mmol) were mixed in 100 mL of tetrahydrofuran and heated to reflux. To the resultant solution 1,3-diisopropylcarbodiimide (8.8 mL, 56.29 mmol) was added dropwise. The mixture was cooled in an ice-bath and the solid was collected by filtration washing with tetrahydrofuran. The filtrate was slowly poured into water and stirred for 30 minutes. The white solid was collected by filtration, washed with water and dried to give 2.58 g of 2-cyano-N-(3,4,5-trimethoxyphenyl)acetamide as a white solid, mp 146-147° C.; $^1$H NMR (400 MHz, DMSO-$d_6$) δ 3.61 (s, 3H), 3.74 (s, 6H), 3.86 (s, 2H), 6.90 (s, 2H), 10.23 (s, 1H); MS (ES) m/z251.1 (M+H)+

Analysis for $C_{12}H_{14}N_2O_4$; Calcd: C, 57.59; H, 5.64; N, 11.19. Found: C, 57.24; H, 5.67; N, 11.08.

EXAMPLE 6

2-(3-Chloropropoxy)-1-methoxy-4-nitrobenzene

A mixture of 2-methoxy-5-nitrophenol (16.90 g, 100 mmol), 3-chloropropyl p-toluenesulfonate (29.2 g, 120 mmol) and potassium carbonate (27.0 g, 195 mmol) in 160 mL of N,N-dimethylformamide was heated at 80° C. for 2 hours. The reaction mixture was cooled to room temperature and partitioned between water and ethyl acetate. The organic layer was washed with saturated sodium bicarbonate, dried over magnesium sulfate and filtered. The solution was concentrated in vacuo and recrystallized from hexane and ethyl acetate to give 4.68 g of 2-(3-chloropropoxy)-1-methoxy-4-nitrobenzene as a first crop of off-white crystals. A second crop of 11.10 g was obtained from the mother liquor. The remaining solution was concentrated in vacuo and purified by flash column chromatography, eluting with 4:1 hexane:ethyl acetate, to provide 1.31 g of 2-(3-chloropropoxy)-1-methoxy-4-nitrobenzene as off-white crystals, mp 85-87° C.; $^1$H NMR (400 MHz, DMSO-$d_6$) δ 2.23 (m, 2H), 3.79 (t, J=6 Hz, 2H), 3.92 (s, 3H), 4.21 (t, J=6 Hz, 2H), 7.19 (d, J=9 Hz, 1H), 7.77 (d, J=2 Hz, 1H), 7.92 (dd, J=9, 2 Hz, 1H); MS (ES) m/z246.1, 248.1 (M+H)+

Analysis for $C_{10}H_{12}ClNO_4$; Calcd: C, 48.89; H, 4.92; N, 5.70. Found: C, 49.09; H, 4.68; N, 5.62.

ALTERNATIVE EXAMPLE 6

2-methoxy-5-nitrophenol (50 g, 0.30 mol) was combined with 250 mL isopropyl alcohol. 1N sodium hydroxide solution, 310 mL (0.31 mol), was added to the mixture at such a rate that the temperature remained below 40° C. After the addition was completed, the mixture was stirred for at least 30 minutes. The reaction was then charged with 1-bromo-3-chloropropane (93.1 g, 0.59 mol) in a single portion. The mixture was heated to 75° C. and monitored periodically by high performance liquid chromatography (HPLC). After 8 hours, heating was discontinued and the reaction mixture was allowed to cool to ambient temperature overnight. The product gradually precipitated from the mixture as a light yellow/tan solid. Water, 200 mL, was added in a single portion and the resulting slurry was stirred for at least 30 minutes. The slurry was filtered and washed with water. The damp crude product was slurried in 650 mL methanol and heated to reflux until the solids had dissolved or mostly dissolved. The solution was allowed to cool gradually with stirring to ambient temperature over 3-5 hours or longer. The mixture was then cooled to 10-15° C. and held for at least 30 minutes. The solids were filtered and washed with cold methanol. The product was then dried in vacuo to give 60.3 g of 2-(3-chloropropoxy)-1-methoxy-4-nitrobenzene.

EXAMPLE 7

3-(3-Chloropropoxy)-4-methoxyaniline

A mixture of 2-(3-chloropropoxy)-1-methoxy-4-nitrobenzene (2.15 g, 8.77 mmol) and tin (II) chloride dihydrate (6.1 g, 27.11 mmol) in 50 mL of ethyl acetate was heated at reflux for 6.5 hours. The reaction mixture was cooled to room temperature and poured into 250 mL of saturated aqueous sodium bicarbonate. After stirring for 40 minutes, additional ethyl acetate was added and the layers were separated. The organic layer was washed with saturated sodium bicarbonate and water then dried over magnesium sulfate and filtered.

The solution was concentrated in vacuo and purified by flash column chromatography, eluting with 1:1 hexane: ethyl acetate, to provide 753 mg of 3-(3-chloropropoxy)-4-methoxyaniline as a dark brown oil; $^1$H NMR (400 MHz, DMSO-$d_6$) δ 2.13 (m, 2H), 3.62 (s, 3H), 3.78 (t, J=6 Hz, 2H), 3.96 (t, J=6 Hz, 2H), 4.77 (br s, 2H), 6.10 (dd, J=8, 2 Hz, 1H), 6.29 (d, J=2 Hz, 1H), 6.66 (d, J=8 Hz, 1H); MS (ES) m/z216.1, 218.1 (M+H)+.

EXAMPLE 8

1-Ethoxy-2-iodo-4-nitrobenzene

A suspension of 2-iodo-4-nitrophenol (21 g, 79.2 mmol) [ref: Kometani, T.; Watt, D. S.; Ji, T., Tetrahedron Lett. (1985), 26(17), 2043], ethyl iodide (9 mL, 0.48 mol) and potassium carbonate (40.7 g, 0.3 mol) in 100 mL of N,N-dimethylformamide was heated at 70° C. for 3 hours. The reaction was cooled to room temperature and ethyl acetate was added. The inorganic salts were filtered and washed with ethyl acetate. The organic material was washed with water (3×) and brine, dried over magnesium sulfate and filtered. Upon concentration of the filtrate a solid appeared. This solid was filtered and washed with hexanes to give 5.2 g of 1-ethoxy-2-iodo-4-nitrobenzene as white crystals. Concentration of the filtrate provided an additional 11.3 g of the desired product, mp 81-83° C.; $^1$H NMR (400 MHz, DMSO-$d_6$) δ 1.42 (t, 3H), 4.26 (q, 2H), 7.18 (d, 1H), 8.26 (dd, 1H), 8.55 (d, 1H)

Analysis for $C_8H_8INO_3$; Theory: C, 32.79; H, 2.75; N, 4.78; Found: C, 32.71; H, 2.58; N, 4.53.

EXAMPLE 9

(4-Ethoxy-3-iodophenyl)amine

A suspension of iron (3.81 g, 70 mmol) and ammonium chloride (5.47 g, 102 mmol) in 80 mL of ethanol and 25 mL of water was heated to reflux. 1-Ethoxy-2-iodo-4-nitrobenzene (5.0 g, 20 mmol) was added in portions and the reaction was heated at reflux for 1 hour. The hot mixture was filtered through Celite, washed with hot ethanol. The filtrate was concentrated in vacuo and treated with ethyl acetate and water. The organic layer was extracted, washed with brine, dried over magnesium sulfate and filtered. Removal of the solvent in vacuo provided 5.1 g of (4-ethoxy-3-iodophenyl) amine as a light brown oil; $^1$H NMR (400 MHz, DMSO-$d_6$) δ 1.30 (s, 3H), 3.89 (q, 2H), 4.82 (bs, 2H), 6.53 (dd, 1H), 6.72 (d, 1H), 7.11 (d, 1H); MS (ES) m/z263.9 (M+H)+

Analysis for $C_8H_{10}INO$; Theory: C, 36.52; H, 3.83; N, 5.32; Found: C, 36.84; H, 3.71; N, 4.96.

EXAMPLE 10

2-Iodo-1-(2-methoxyethoxy)-4-nitrobenzene

A suspension of 2-iodo-4-nitrophenol (15.5 g, 58.7 mmol) [ref: Kometani, T.; Watt, D. S.; Ji, T., Tetrahedron Lett. (1985), 26(17), 2043], 2-chloroethyl methyl ether (10.69 mL, 117 mmols), potassium carbonate (16.8 g, 117 mmol) and sodium iodide (100 mg) in 160 mL of N,N-dimethylformamide was heated at 70-80° C. for 4 hours. An additional 5.35 mL of 2-chloroethyl methyl ether was added and the reaction was heated until thin layer chromatography (TLC) showed the absence of the phenol. The mixture was filtered and the filtrate was concentrated in vacuo. The solid was partitioned between ethyl acetate and 1 N sodium hydroxide. The organic layer was dried over magnesium sulfate, filtered and concentrated in vacuo. The residue was purified by column chromatography eluting with a gradient of hexane to 50% ethyl acetate in hexane. The resultant oil was recrystallized from ether to provide 7.5 g of 2-iodo-1-(2-methoxyethoxy)-4-nitrobenzene as a white solid, mp 35-36° C.; $^1$H NMR (300 MHz, DMSO-$d_6$) δ 3.37 (s, 3H), 3.74 (t, 2H), 4.33 (t, 2H), 7.20 (d, 1H), 8.26 (d, 1H), 8.56 (s, 1H)

Analysis for $C_9H_{10}INO_4$; Theory: C, 33.46; H, 3.12; N, 4.34; Found: C, 34.39; H, 3.11; N, 4.41.

EXAMPLE 11

[3-Iodo-4-(2-methoxyethoxy)phenyl]amine

A suspension of iron (3.89 g, 69.7 mmol), ammonium chloride (5.0 g, 93.5 mmol), in 100 mL of ethanol and 28 mL of water was heated to reflux. 2-Iodo-1-(2-methoxyethoxy)-4-nitrobenzene (7.5 g, 23.2 mmol) was added and the reaction was heated at reflux for 3 hours. The mixture was cooled to room temperature and filtered through Celite, washed with ethanol. The filtrate was concentrated in vacuo until a precipitate appeared. The precipitate was removed by filtration through Magnesol and the filtrate was concentrated in vacuo to provide 4.0 g of [3-iodo-4-(2-methoxyethoxy) phenyl]amine as an oil; $^1$H NMR (300 MHz, DMSO-$d_6$) δ 3.33 (s, 3H), 3.62 (t, 2H), 3.95 (t, 2H), 5.01 (d, 2H), 6.55 (d, 1H), 6.73 (d, 1H), 7.03 (s, 1H); MS (ES) m/z294.0 (M+H)

Analysis for $C_9H_{12}INO_2$; Theory: C, 36.88; H, 4.13; N, 4.78; Found: C, 37.28; H, 4.29; N, 4.80.

EXAMPLE 12

3,4-Dimethoxyanilino-N-(dimethyl)-2-cyano-2-propenamide 3,4-Dimethoxyaniline (1.50 g, 0.010 mol), dimethylaminocyanoacetamide (1.50 g, 0.013 mol) and triethylorthoformate (2 mL, 0.012 mol) were mixed in ethylene glycol (10 mL) and the solution heated to reflux. The solution was stirred for 5 hours then allowed to cool to room temperature when precipitate was formed. Water (120 mL) was added and the suspension filtered. The wet solids were suspended in dichloromethane (100 mL), stirred with magnesium sulfate, filtered and concentrated to provide 3,4-dimethoxyanilino-N-(dimethyl)-2-cyano-2-propenamide as a grey solid (1.54 g, 57% yield, 88% purity by GC). $^1$H NMR (300 MHz, DMSO-$d_6$): 10.9 (d, J=21 Hz, 1H), 8.23 (d, J=21 Hz, 1H), 7.08 (s, 1H), 6.9-6.9 (m, 2H), 3.78 (s, 3H), 3.72 (s, 3H), 3.03 (bs, 6H).

EXAMPLE 13

3,4-Dimethoxyanilino-N-(3-chloro-4-fluorophenyl)-2-cyano-2-propenamide 3,4-Dimethoxyaniline (0.30 g, 0.002 mol) and (3-chloro-4-fluoro)-2-cyanoacetamide (0.50 g, 0.0024 mol) and triethylorthoformate (2 mL, 0.012 mol) were mixed in ethylene glycol (4 ml) and heated to reflux. The solution was stirred for 1.5 hours then allowed to cool to ~50° C. and water (15 mL) was added. The suspension was allowed to cool to room temperature and the solids isolated by filtration, washed with MTBE (2×15 mL) to provide 3,4-dimethoxyanilino-N-(3-chloro-4-fluorophenyl)-2-cyano-2-propenamide as a beige solid (0.55 g, 93% purity by LCMS): $^1$H NMR, DMSO-d$_6$): 11.3 (d, J=15 Hz , 1H), 9.76 (s, 1H), 8.70 (d, J=15 Hz, 1H), 7.97 (d, J=8 Hz, 1H), 7.6-7.57 (m, 1H), 7.51 (d, J=9 Hz, 1H), 7.3 (t, J=9 Hz, 1H), 7.29 (s, 1H), 6.97 (d, J=8 Hz, 1H), 3.72 (s, 3H), 3.03 (bs, 6H).

EXAMPLE 14

4-Bromo-3-ethoxyanilino-(N-3-chloro-4-fluorophenyl)-2-cyano-2-propenamide

A 2-L round-bottomed flask under N$_2$ equipped with an overhead stirrer, a condenser, thermocouple and 100 mL dropping funnel were charged with (3-chloro-4-fluoro)-2-cyanoacetamide (100 g, 0.47 mol), 4-bromo-3-ethoxyaniline hydrochloride (100.4 g, 0.40 mol) and iso-propanol (500 mL). Triethylorthoformate (64 mL, 57 g, 0.38 mol) was added and the suspension heated to 72° C. After 1.5 hours a further aliquot of triethylorthoformate (64 mL, 57 g, 0.38 mol) was added and the reflux continued. After a further 2 hours at reflux a third aliquot of triethylorthoformate (64 mL, 57 g, 0.38 mol) was added and heat continued for 10 hours. The reaction mixture was cooled to 20-25° C. and the precipitate collected by filtration. The filter cake was washed with iso-propanol (2×100 mL) and dried under vacuum (45° C., 50 mm Hg) to provide 4-bromo-3-ethoxyanilino-(N-3-chloro-4-fluorophenyl)-2-cyano-2-propenamide as an off-white solid (136.5 g, 70% yield, >97.5% purity by HPLC mp 226-228° C.). $^1$H NMR, DMSO-d$_6$): 11.3 (d, J=15 Hz, 1H), 9.76 (s, 1H), 8.70 (d, J=15 Hz, 1H), 7.97 (d, J=8 Hz, 1H), 7.6-7.57 (m, 1H), 7.51 (d, J=9 Hz, 1H), 7.38 (t, J=9 Hz, 1H), 7.29 (s, 1H), 6.97 (d, J=8 Hz, 1H), 4.14 (q, J=9 Hz, 2H), 1.37 (t, J=9 Hz, 3H).

EXAMPLE 15

3-Fluoro-4-methoxyanilino-N-(2,4-dichloro-5-methoxyphenyl)-2-cyano-2-propenamide To a suspension of 2-cyano-N-(2,4-dichloro-5-methoxyphenyl)acetamide (1.00 g, 3.86 mmol) in 200 mL of isopropanol was added 3-fluoro-p-anisidine (0.60 g, 4.25 mmol). This mixture was heated to reflux to give a clear yellow solution. To this solution, triethylorthoformate (1.72 mL, 10.34 mmol) was added dropwise and the reaction mixture was heated at reflux overnight. An additional 2 mL of triethylorthoformate was added and the mixture was heated at reflux overnight. An additional 2 mL of triethylorthoformate was added and the mixture was heated at reflux overnight. The mixture was allowed to cool to room temperature and the white solid was collected by filtration, washed with isopropanol, and dried overnight at ~40° C. under reduced pressure. Purification by suspension in hot ethyl acetate followed by addition of cold hexanes gave 1.08 g (68%) of 3-fluoro-4-methoxyanilino-N-(2,4-dichloro-5-methoxyphenyl)-2-cyano-2-propenamide as a white solid, mp 275-276° C.; MS 408.1, 410.1 (M–H)–

Analysis for C$_{18}$H$_{14}$Cl$_2$FN$_3$O$_3$; Calcd: C, 52.70; H, 3.44; N, 10.24. Found: C, 52.44; H, 3.26; N, 10.14.

EXAMPLE 16

3-(3-Chloropropoxy)-4-methoxyanilino-N-(2,4-dichloro-5-methoxyphenyl)-2-cyano-2-propenamide To a suspension of 2-cyano-N-(2,4-dichloro-5-methoxyphenyl)acetamide (738 mg, 2.84 mmol) in 100 mL of isopropanol was added 3-(3-chloropropoxy)-4-methoxyaniline (611 mg, 2.84 mmol). This mixture was heated to reflux and triethylorthoformate (3.0 mL, 18.0 mmol) was added dropwise. The reaction mixture was heated at reflux overnight. The mixture was filtered while still warm and the collected white solid was washed with isopropanol to give 610 mg of 3-(3-chloropropoxy)-4-methoxyanilino-N-(2,4-dichloro-5-methoxyphenyl)-2-cyano-2-propenamide, mp 185-192° C.; MS (ES) m/z 482.1, 484.2, 486.0 (M–H)–

Analysis for C$_{21}$H$_{20}$Cl$_3$N$_3$O$_4$; Calcd: C, 52.03; H, 4.16; N, 8.67. Found: C, 51.89; H, 4.11; N, 8.53.

EXAMPLE 17

3-Bromo-4-methoxyanilino-N-(2,4-dichloro-5-methoxyphenyl)-2-cyano-2-propenamide

To a suspension of 2-cyano-N-(2,4-dichloro-5-methoxyphenyl)acetamide (900 mg, 3.46 mmol) in 100 mL of iso-propanol was added 3-bromo-4-methoxyaniline (700 mg, 3.46 mmol). This mixture was heated to reflux and triethylorthoformate (3.3 mL, 19.8 mmol) was added dropwise. The reaction mixture was heated at reflux for 6 hours. The mixture was filtered while still warm and the collected white solid was washed with iso-propanol to give 376 mg of 3-bromo-4-methoxyanilino-N-(2,4-dichloro-5-methoxyphenyl)-2-cyano-2-propenamide, mp >250° C.; MS (ES) m/z 467.7, 469.9, 471.7 (M–H)–

Analysis for C$_{18}$H$_{14}$BrCl$_2$N$_3$O$_3$; Calcd: C, 45.89; H, 3.00; N, 8.92. Found: C, 45.75; H, 2.77; N, 8.78.

EXAMPLE 18

3-Bromo-4-ethoxyanilino-N-(2,4-dichloro-5-methoxyphenyl)-2-cyano-2-propenamide

To a suspension of 2-cyano-N-(2,4-dichloro-5-methoxyphenyl)acetamide (715 mg, 2.74 mmol) in 50 mL of iso-propanol was added 3-bromo-4-ethoxyaniline (586 mg, 2.71 mmol). This mixture was heated to reflux and triethylorthoformate (2.7 mL, 16.2 mmol) was added dropwise. The reaction mixture was heated at reflux overnight. The mixture was filtered while still warm and the collected white solid was washed with iso-propanol to give 666 mg of 3-bromo-4-ethoxyanilino-N-(2,4-dichloro-5-methoxyphenyl)-2-cyano-2-propenamide, mp >250° C.; MS (ES) m/z 482.0, 484.0, 486.0 (M–H)–

Analysis for C$_{19}$H$_{16}$BrCl$_2$N$_3$O$_3$; Calcd: C, 47.04; H, 3.32; N, 8.66. Found: C, 46.64; H, 3.40; N, 8.59.

EXAMPLE 19

4-Bromo-3-methoxyanilino-N-(2,4-dichloro-5-methoxyphenyl)-2-cyano-2-propenamide

To a suspension of 2-cyano-N-(2,4-dichloro-5-methoxyphenyl)acetamide (6.1 g, 23.5 mmol) in 500 mL of isopropanol was added 5-amino-2-bromoanisole (5.0 g, 24.8 mmol). This mixture was heated to reflux to give a clear yellow solution. To this solution, triethylorthoformate (10.6 mL, 63.5 mmol) was added dropwise and the reaction mixture was heated at reflux for 5 hours. An additional 10.6 mL of triethylorthoformate was added and the mixture was heated at reflux overnight. The mixture was allowed to cool to room temperature. The solid was collected by filtration, washed with isopropanol and ethyl acetate, and then dried overnight at ~40° C. under reduced pressure to give 8.1 g (73%) of 4-bromo-3-methoxyanilino-N-(2,4-dichloro-5- methoxyphenyl)-2-cyano-2-propenamide as a yellow solid, mp >250° C.; MS (ES) m/z470.0, 472.0 (M+H)+

Analysis for $C_{18}H_{14}BrCl_2N_3O_3$; Calcd: C, 45.89; H, 3.00; N, 8.92.

EXAMPLE 20

2-Cyano-N-(2,4-dichloro-5-methoxyphenyl)-3-[(3-iodo-4-methoxyphenyl)amino]prop-2-enamide To a suspension of 2-cyano-N-(2,4-dichloro-5-methoxyphenyl)acetamide (5.00 g, 19.30 mol) in 400 mL of iso-propanol, under $N_2$, was added 3-iodo-p-anisidine (5.80 g, 23.16 mmol). This mixture was heated to reflux to give a clear yellow solution. To this solution, triethylorthoformate (8.60 mL, 52.11 mmol) was added dropwise and the reaction mixture was heated at reflux overnight. An additional 10 mL of triethylorthoformate was added and the mixture was heated at reflux overnight. The mixture was allowed to cool to room temperature and the white solid was collected by filtration, washed with isopropanol, and dried overnight at ~40° C. under reduced pressure. Purification by suspension in hot ethyl acetate followed by addition of cold hexanes gave 8.50 g (85%) of 2-cyano-N-(2,4-dichloro-5-methoxyphenyl)-3-[(3-iodo-4-methoxyphenyl)amino]prop-2-enamide as a yellow solid, mp 289-290° C.; MS (ES) m/z 516.7 (M–H)–

Analysis for $C_{18}H_{14}Cl_2IN_3O_3$; Calcd: C, 41.73; H, 2.72; N, 8.11. Found: C, 40.66; H, 2.94; N, 7.90.

EXAMPLE 21

4-Ethoxy-3-fluoroanilino-N-(2,4-dichloro-5-methoxyphenyl)-2-cyano-2-propenamide

To a suspension of 2-cyano-N-(2,4-dichloro-5-methoxyphenyl)acetamide (5.9 g, 22.7 mmol) in 400 mL of isopropanol was added 4-ethoxy-3-fluoroaniline (3.7 g, 23.8 mmol). This mixture was heated to reflux to give a clear solution. To this solution, triethylorthoformate (11.6 mL, 69.6 mmol) was added dropwise and the reaction mixture was heated at reflux for 18 hours. Additional triethylorthoformate (11.6 mL, 69.6 mmol) was added dropwise and the reaction mixture was heated at reflux for 42 hours. The mixture was allowed to cool to room temperature and the solid was collected by filtration, washed with ethyl acetate, and dried in vacuo at 40° C. to give 6.4 g (67%) of 4-ethoxy-3-fluoroanilino-N-(2,4-dichloro-5-methoxyphenyl)-2-cyano-2-propenamide as a grey solid, mp 245-247° C.; MS 424.1, 426.1 (M+H)+

Analysis for $C_{19}H_{16}Cl_2FN_3O_3$; Calcd: C, 53.79; H, 3.80; N, 9.90. Found: C, 53.39; H, 3.97; N, 9.69.

EXAMPLE 22

2-Cyano-N-(2,4-dichloro-5-methoxyphenyl)-3-(thien-3-ylamino)prop-2-enamide

To a suspension of 2-cyano-N-(2,4-dichloro-5-methoxyphenyl)acetamide (1.57 g, 6.06 mmol) in 200 mL of iso-propanol was added 3-aminothiophene (600 mg, 6.06 mmol). This mixture was heated to reflux and triethylorthoformate (6.5 mL, 39.1 mmol) was added dropwise. The reaction mixture was heated at reflux overnight. Additional 3-aminothiophene (214 mg, 2.16 mmol) was added and the reaction mixture was heated at reflux for 5 hours. Additional 3-aminothiophene (100 mg, 1.01 mmol) was added and the reaction mixture was heated at reflux for 2.5 hours. The mixture was allowed to cool to room temperature and the solid was collected by filtration, washed with iso-propanol to give 572 mg (26%) of 2-cyano-N-(2,4-dichloro-5-methoxyphenyl)-3-(thien-3-ylamino)prop-2-enamide as a tan solid, mp >250° C.; MS 366.0, 368.2 (M–H)–

Analysis for $C_{15}H_{11}Cl_2N_3O_2S$-1.0 $H_2O$; Calcd: C, 46.64; H, 3.39; N, 10.88. Found: C, 46.37; H, 2.94; N, 10.60.

EXAMPLE 23

2-Cyano-N-(2,4-dichloro-5-methoxyphenyl)-3-[(4-ethoxy-3-iodophenyl)amino]acrylamide To a suspension of 2-cyano-N-(2,4-dichloro-5-methoxyphenyl)acetamide (5.44 g, 21.0 mmol) in 350 mL of iso-propanol, under $N_2$, was added (4-ethoxy-3-iodophenyl)amine (5.0 g, 19.30 mmol). This mixture was heated to reflux and triethylorthoformate (8.53 mL, 51.30 mmol) was added dropwise and the reaction mixture was heated at reflux overnight. The mixture was allowed to cool to room temperature and the yellow solid was collected by filtration, washed with iso-propanol, and dried overnight at ~40° C. under reduced pressure to give 5.46 g (54%) of 2-cyano-N-(2,4-dichloro-5-methoxyphenyl)-3-[(4-ethoxy-3-iodophenyl)amino]prop-2-enamide as a yellow solid, mp >245° C.; MS (EI) m/z 531.01 (M)+

Analysis for $C_{19}H_{16}Cl_2IN_3O_3$; Calcd: C, 42.88; H, 3.03; N, 7.90. Found: C, 42.99; H, 2.97; N, 7.74.

EXAMPLE 24

2-Cyano-N-(2,4-dichloro-5-methoxyphenyl)-3-{[3-iodo-4-(2-methoxyethoxy)phenyl]amino}acrylamide A suspension of 2-cyano-N-(2,4-dichloro-5-methoxyphenyl)acetamide (3.2 g, 12.4 mmol) and [3-iodo-4-(2-methoxyethoxy)phenyl]amine (4.0 g, 13.7 mmol) in 350 mL of iso-propanol was heated to reflux and triethylorthoformate (5.6 mL, 33.7 mmol) was added dropwise. The reaction mixture was heated at reflux for 3 hours. Additional triethylorthoformate (2.0 mL, 12.0 mmol) was added dropwise and the reaction mixture was heated at reflux overnight. The mixture was allowed to cool to room temperature and the solid was collected by filtration, washed with iso-propanol, diethyl ether, and ethyl acetate and then dried in vacuo to give 5.5 g of 2-cyano-N-(2,4-dichloro-5-methoxyphenyl)-3-{[3-iodo-4-(2-methoxyethoxy)phenyl]amino}acrylamide as a yellow solid, mp 209-210° C.; MS (ES) 560.0, 562.1 (M–H)–

Analysis for $C_{20}H_{18}Cl_2IN_3O_4$; Calcd: C, 42.73; H, 3.23; N, 7.47. Found: C, 43.04; H, 3.07; N, 7.28.

EXAMPLE 25

2-Cyano-N-(2,4-dichloro-5-methoxyphenyl)-3-[(3-bromo)phenyl)amino]acrylamide

A suspension of 2-cyano-N-(2,4-dichloro-5-methoxyphenyl)acetamide (3.0 g, 11.5 mmol) and 3-bromoaniline (1.3 mL, 11.9 mmol) in 250 mL of iso-propanol was heated to reflux and triethylorthoformate (12 mL, 72.2 mmol) was added dropwise. The reaction mixture was heated at reflux overnight. The mixture was allowed to cool slightly and the solid was collected by filtration while still warm, washed with iso-propanol and diethyl ether to give 2.05 g of 2-cyano-N-(2,4-dichloro-5-methoxyphenyl)-3-[(3-bromo)

phenyl)amino]acrylamide as a yellow solid, mp >250° C.; MS (ES) 437.8, 439.7, 441.8 (M–H)–

Analysis for $C_{17}H_{12}BrCl_2N_3O_2$; Calcd: C, 46.29; H, 2.74; N, 9.53. Found: C, 46.33; H, 2.73; N, 9.40.

EXAMPLE 26

6-Bromo-[7-ethoxy-4-(3-chloro-4-fluorophenyl) amino]-3-quinolinecarbonitrile

A 22-L round-bottomed flask under $N_2$ equipped with overhead stirrer, thermocouple, condenser and 1000 mL dropping funnel was charged with 4-bromo-3-ethoxyanilino-(N-3-chloro-4-fluorophenyl)-2-cyano-2-propenamide (1000 g, 2.29 mol) methanol (40 mL) and acetonitrile (7.50 L). The suspension was heated to 80-82° C. Phosphorus oxychloride (740 g, 4.83 mol) was charged to the dropping funnel and added over 30 minutes. The suspension was refluxed for 24 hours until <3% starting material was present by HPLC. The mixture was cooled to 0-10° C. and filtered. The filter cake was washed with acetonitrile (3×0.63 kg) and the filter cake dried on the filter funnel for 2 hours. A 50-L round-bottomed flask equipped with overhead stirrer, thermocouple, condenser and 1000 mL dropping funnel was charged with the filter cake from above. THF (4.44 kg) was added and the suspension warmed to 35-40° C. 28% Ammonium hydroxide (0.63 kg) and water (2 kg) were mixed in a flask and transferred to the dropping funnel. The ammonium hydroxide solution was added to the THF suspension over 30 minutes maintaining the temperature below 55° C. Water (10 kg) was added over 25 minutes then the resulting suspension was cooled to 15-20° C. The precipitate was collected by filtration then washed with hot water (3×1 kg), acetonitrile (2×1 kg) and dried under vacuum (55 mm Hg, 65° C.) to provide 6-bromo-[7-ethoxy-4-(3-chloro-4-fluorophenyl)amino]-3-quinolinecarbonitrile as an orange-yellow solid (806 g, 84% yield, >96% purity by HPLC mp 213-215° C.). $^1H$ NMR (300 MHz, $CDCl_3$): 8.7 (s, 1H), 7.99 (s, 1H), 7.40-6.91 (m, 5H), 4.18 (q, J=7.5 Hz, 2H), 1.56 (t, J=7.5 Hz, 3H).

EXAMPLE 27

6-Bromo-[7-ethoxy-4-(3-chloro-4-fluorophenyl) amino]-3-quinolinecarbonitrile

A 250-mL round-bottomed flask under $N_2$ equipped with overhead stirrer, thermocouple, condenser and 10 mL dropping funnel was charged with 4-bromo-3-ethoxyanilino-(N-3-chloro-4-fluorophenyl)-2-cyano-2-propenamide (10.0 g, 0.023 mol) pyridine (3.80 g, 0.048 mol) and toluene (100 ml). The suspension was heated to 110° C. Phosphorus oxychloride (4.4 mL, 0.047 mol) was charged to the dropping funnel and added over 3.75 hours. Heat was continued for 0.25 hours until <3% starting material was present by HPLC then the suspension allowed to cool to room temperature. Water (50 mL) was added to the reaction mixture as a slow stream then the mixture basified by the addition of 50% aq, sodium hydroxide solution. The suspension was cooled to 10-15° C. and the precipitate was collected by filtration then washed with water (2×10 mL), toluene (2×10 ml)) and dried under vacuum (55 mm Hg, 65° C.) to provide 6-bromo-[7-ethoxy-4-(3-chloro-4-fluorophenyl)amino]-3-quinolinecarbonitrile as an orange-yellow solid (6.90 g, 72% yield, >92.2% purity by HPLC). $^1H$ NMR (300 MHz, $CDCl_3$): 8.7 (s, 1H), 7.99 (s, 1H), 7.40-6.91 (m, 5H), 4.18 (q, J=7.5 Hz, 2H), 1.56 (t, J=7.5 Hz, 3H).

EXAMPLE 28

6-Bromo-[7-ethoxy-4-(3-chloro-4-fluorophenyl) amino]-3-quinolinecarbonitrile

A 5-L round-bottomed flask under $N_2$ equipped with overhead stirrer, thermocouple, condenser and 500 mL dropping funnel was charged with 4-bromo-3-ethoxyanilino-(N-3-chloro-4-fluorophenyl)-2-cyano-2-propenamide (500 g, 1.14 mol) 1-butanol (15 g, 0.20 mol) and toluene (3.5 L). The suspension was heated to 105-108° C. Phosphorus oxychloride (370 g, 2.41 mol) was charged to the dropping funnel and added to the suspension over 10 hours. Heat was continued for further 16 hours until <3% starting material was present by HPLC. The mixture was cooled to 0-10° C. and filtered. The filter cake was washed with toluene (2×0.3 kg) and the filter cake dried on the filter funnel for 2 hours.

A 12-L round-bottomed flask equipped with overhead stirrer, thermocouple, condenser and 1000 mL dropping funnel was charged with the filter cake from above. THF (2.22 kg) was added and the suspension warmed to 35-40° C. 28% Ammonium hydroxide (0.63 kg) and water (1 kg) were mixed in a flask and transferred to the dropping funnel. The ammonium hydroxide solution was added to the THF suspension over 30 minutes maintaining the temperature below 55° C. Water (5 kg) was added over 25 minutes then the resulting suspension was cooled to 15-20° C. The precipitate was collected by filtration then washed with hot water (3×1 kg), acetonitrile (2×0.4 kg) and dried under vacuum (55 mm Hg, 65° C.) to provide 6-Bromo-[7-ethoxy-4-(3-chloro-4-fluorophenyl)amino]-3-quinolinecarbonitrile as an orange-yellow solid (389.1 g, 81% yield, >97.5% purity by HPLC). $^1H$ NMR (300 MHz, $CDCl_3$): 8.7 (s, 1H), 7.99 (s, 1H), 7.40-6.91 (m, 5H), 4.18 (q, J=7.5 Hz, 2H), 1.56 (t, J=7.5 Hz, 3H)

Analysis for $C_{18}H_{12}BrClFN_3O$; Calcd: C, 51.39; H, 2.88; N, 9.99. Found: C, 51.50; H, 2.75; N, 10.09.

EXAMPLE 29

6,7-Dimethoxy-4-(N,N-dimethylamino)-3-quinolinecarbonitrile

A suspension of 3,4-dimethoxyanilino-N-(dimethyl)-2-cyano-2-propenamide (0.500 g, 1.82 mmol) in acetonitrile (10 mL) was treated with phosphorus oxychloride (0.17 mL, 0.28 g, 1.82 mmol) and heated to reflux. The mixture was stirred for 1 hour and an additional aliquot of phosphorus oxychloride (0.17 mL, 0.28 g, 1.82 mmol) added. The mixture was heated at reflux for 8 hours then stirred at room temperature for 24 hours. The resultant solution was concentrated in vacuo and stirred with aqueous sodium carbonate solution. The mixture was extracted with methylene chloride (3×30 mL), the combined extracts were dried over magnesium sulfate, filtered and concentrated in vacuo to produce 6,7-dimethoxy-4-(N,N-dimethylamino)-3-quinolinecarbonitrile as a tan solid (0.37 g, 79%, 89% purity by GC).

EXAMPLE 30

6,7-Dimethoxy-4-[(3-chloro-4-fluorophenyl)amino]-3-quinolinecarbonitrile

A suspension of 3,4-dimethoxy-N-(3-chloro-4-fluorophenyl)-2-cyano-2-propenamide (0.84 g, 2.23 mmol) in acetonitrile (10 mL) was treated with phosphorus oxychloride (0.42 mL, 0.68 g, 4.50 mmol) and heated to reflux for 8 hours. The suspension was cooled to room temperature and stirred with saturated sodium carbonate solution (70 mL). The mixture was extracted with methylene chloride (3×70 mL), the combined extracts were dried over magnesium sulfate, filtered and concentrated in vacuo to produce 6,7-dimethoxy-4-[(3-chloro-4-fluorophenyl)amino]-3-quinolinecarbonitrile as brown solid (0.74 g, 93%, 95% by LC-MS 1.3% isomer by LC-MS). $^1$H NMR (300 MHz, DMSO-$d_6$).

EXAMPLE 31

4-[(2,4-Dichloro-5-methoxyphenyl)amino]-6-ethoxy-7-fluoro-3-quinolinecarbonitrile A suspension of 4-ethoxy-3-fluoroanilino-N-(2,4-dichloro-5-methoxyphenyl)-2-cyano-2-propenamide (6.28 9, 14.8 mmol) in 54 mL of acetonitrile and 2.0 mL of methanol was heated to reflux and phosphorous oxychloride (8.3 mL, 88.8 mmol) was added dropwise. The mixture was heated at reflux for 17 hours. The resultant solution was concentrated in vacuo and acetonitrile was added to the residue. The solid was collected by filtration, washed with acetonitrile. The solid was suspended in tetrahydrofuran and neutralized with concentrated ammonium hydroxide. After stirring for 30 minutes, water was added and the mixture was stirred for 1 hour. The solid was collected by filtration, washed with water, followed by 1:1 diethyl ether and hexane. The light yellow solid was dried in vacuo to provide 2.2 g (37%) of 4-[(2,4-dichloro-5-methoxyphenyl)amino]-6-ethoxy-7-fluoro-3-quinolinecarbonitrile, mp 185-187° C.; $^1$H NMR (400 MHz, DMSO-$d_6$) δ 1.95 (t, J=7 Hz, 3H), 3.87 (s, 3H), 4.29 (q, J=7 Hz, 2H), 7.39 (s, 1H), 7.66-7.81 (m, 2H), 8.09 (d, J=9 Hz, 1H), 8.49 (s, 1H), 9.80 (s, 1H); MS (ES) m/z 406.1, 408.2 (M+H)+

Analysis for $C_{19}H_{14}Cl_2FN_3O_2$-0.4 $H_2O$; Calcd: C, 55.20; H, 3.61; N, 10.16. Found: C, 55.25; H, 3.53; N, 10.15.

EXAMPLE 32

4-[(2,4-Dichloro-5-methoxyphenyl)amino]-7-fluoro-6-methoxy-3-quinolinecarbonitrile To a suspension of 3-fluoro-4-methoxyanilino-N-(2,4-dichloro-5-methoxyphenyl)-2-cyano-2-propenamide (360 mg, 0.88 mmol) in 40 mL of acetonitrile was added 0.1 mL of methanol. The reaction mixture was heated to reflux and phosphorous oxychloride (0.65 mL, 7.0 mmol) was added dropwise, via syringe. After 2 hours the mixture became a clear orange solution. This solution was heated at reflux overnight. After 24 hours, the reaction mixture was cooled in an ice-bath and the solid was collected by filtration, washed with cold acetonitrile (20 mL) and then suspended in tetrahydrofuran (50 mL). To both the acetonitrile filtrate and the tetrahydrofuran suspension were added concentrated ammonium hydroxide (2×25 mL) and the mixtures were stirred for 1 hour. Water (2×400 mL) was added and stirring was continued for 2 hours. The resulting solids were combined, washed with hot water and dried under reduced pressure at ~40° C., overnight, to provide 189 mg (55%) of 4-[(2,4-dichloro-5-methoxyphenyl)amino]-7-fluoro-6-methoxy-3-quinolinecarbonitrile as orange crystals, mp 219-221° C.; $^1$H NMR (400 MHz, DMSO-$d_6$) δ 3.87 (s, 3H), 4.02 (s, 3H), 7.36 (s, 1H), 7.65-7.80 (m, 2H), 8.08 (d, J=9 Hz, 1H), 8.48 (s, 1H), 9.85 (s, 1H); MS (ES) m/z392.0, 394.0 (M+H)+

Analysis for $C_{18}H_{12}Cl_2FN_3O_2$-0.5 $H_2O$; Calcd: C, 53.88; H, 3.27; N, 10.48. Found: C, 54.09; H, 3.20; N, 10.24.

EXAMPLE 33

7-(3-Chloropropoxy)-4-[(2,4-dichloro-5-methoxyphenyl)amino]-6-methoxy-3-quinolinecarbonitrile A suspension of 3-(3-chloropropoxy)-4-methoxyanilino-N-(2,4-dichloro-5-methoxyphenyl)-2-cyano-2-propenamide (462 mg, 0.95 mmol) in 40 mL of acetonitrile was heated to reflux and phosphorous oxychloride (0.60 mL) was added dropwise, via syringe. The reaction mixture was heated at reflux overnight, then cooled to room temperature and concentrated in vacuo. The residue was cooled to 0° C. and saturated aqueous sodium bicarbonate was added. The mixture was stirred for 10 minutes and the solid was collected by filtration, washed with water. The solid was suspended in hot ethyl acetate and methanol and then filtered to provide 200 mg of 7-(3-chloropropoxy)-4-[(2,4-dichloro-5-methoxyphenyl)amino]-6-methoxy-3-quinolinecarbonitrile as a pale yellow solid. $^1$H NMR (400 MHz, DMSO-$d_6$) δ 2.30 (m, 2H), 3.84 (t, J=6 Hz, 1H), 3.88 (s, 3H), 4.01 (s, 3H), 4.32 (t, J=6 Hz, 2H), 7.46 (s, 1H), 7.51 (s, 1H), 7.81 (s, 1H), 8.14 (s, 1H), 8.81 (s, 1H), 10.83 (br s, 1H), MS (ES) m/z 466.1, 468.1 (M+H)+.

EXAMPLE 34

7-Bromo-4-[(2,4-dichloro-5-methoxyphenyl)amino]-6-methoxy-3-quinolinecarbonitrile A suspension of 3-bromo-4-methoxyanilino-N-(2,4-dichloro-5-methoxyphenyl)-2-cyano-2-propenamide (4.00 g, 8.50 mmol) in 200 mL of acetonitrile was heated to reflux and phosphorous oxychloride (5.0 mL) was added dropwise, via syringe. The reaction mixture was heated at reflux overnight, then cooled to room temperature and concentrated in vacuo. The residue was cooled to 0° C. and saturated aqueous sodium bicarbonate was added. The mixture was stirred for 1 hour and then extracted with a large volume of ethyl acetate. The organic layer was washed with saturated aqueous sodium bicarbonate, dried over magnesium sulfate and filtered. The filtrate was reduced in volume until solids appeared. The solids were collected by filtration, washed with diethyl ether and hexanes to provide 1.73 g of 7-bromo-4-[(2,4-dichloro-5-methoxyphenyl)amino]-6-methoxy-3-quinolinecarbonitrile as a light tan solid, mp >250° C. $^1$H NMR (400 MHz, DMSO-$d_6$) δ 3.87 (s, 3H), 4.04 (s, 3H), 7.41 (s, 1H), 7.78 (s, 1H), 7.99(s, 1H), 8.22 (s, 1H), 8.48 (s, 1H), 9.93 (s, 1H); MS (ES) m/z449.9, 451.9, 453.9 (M−H)−

Analysis for $C_{18}H_{12}BrCl_2N_3O_2$; Calcd: C, 47.71; H, 2.67; N, 9.27. Found: C, 47.94; H, 2.74; N, 9.03.

EXAMPLE 35

7-Bromo-4-[(2,4-dichloro-5-methoxyphenyl)amino]-6-ethoxy-3-quinolinecarbonitrile A suspension of 3-bromo-4-ethoxyanilino-N-(2,4-dichloro-5-methoxyphenyl)-2-cyano-2-propenamide (630 mg, 1.29 mmol) in 35 mL of acetonitrile was heated to reflux and phosphorous oxychloride (0.80 mL) was added dropwise, via syringe. The reaction mixture was heated at reflux overnight, then cooled to room temperature. The solids were collected by filtration, washed with saturated aqueous sodium bicarbonate. The solids were stirred with saturated aqueous sodium bicarbonate for 1 hour and then collected by filtration, washed with saturated sodium bicarbonate and water. The solid was recrystallized from methanol and dried in vacuo to provide 225 mg of 7-bromo-4-[(2,4-dichloro-5-methoxyphenyl)amino]-6-ethoxy-3-quinolinecarbonitrile as a yellow solid, mp >250° C. $^1$H NMR (400 MHz, DMSO-d$_6$) δ 1.47 (t, J=7 Hz, 3H), 3.87 (s, 3H), 4.32 (q, J=7 Hz, 2H), 7.45 (s, 1H), 7.82 (s, 1H), 8.16(s, 1H), 8.27 (s, 1H), 8.76 (s, 1H), 10.73 (s, 1H); MS (ES) m/z 466.1, 468.0, 470.1 (M+H)+

Analysis for $C_{19}H_{14}BrCl_2N_3O_2$: 2.0 $H_2O$; Calcd: C, 45.35; H, 3.61; N, 8.35. Found: C, 44.97; H, 3.17; N, 8.07.

EXAMPLE 36

6-Bromo-4-[(2,4-dichloro-5-methoxyphenyl)amino]-7-methoxy-3-quinolinecarbonitrile To a suspension of (5.13 g, 11 mmol) of 4-bromo-3-methoxyanilino-N-(2,4-dichloro-5-methoxyphenyl)-2-cyano-2-propenamide in 400 mL of acetonitrile was added 1.5 mL of methanol. The mixture was heated to reflux and phosphorous oxychloride (4.10 mL, 44.0 mmol) was added dropwise. The resulting mixture was heated at reflux for 26 hours. Additional phosphorous oxychloride (2.1 mL) and methanol (0.75 mL) were added and the mixture was heated at reflux for 21 hours. After cooling to 0-5° C. in an ice-bath, the solid was collected by filtration, washed with cold acetonitrile (100 mL) and then suspended in tetrahydrofuran (100 mL). To the tetrahydrofuran suspension was added concentrated ammonium hydroxide and the mixtures were stirred for 1 hour. Water (300 mL) was added and stirring was continued for 1 hour. The solid was collected by filtration, washed with hot water (46° C.), acetonitrile and dried in vacuo overnight to recover 2.1 g of 4-bromo-3-methoxyanilino-N-(2,4-dichloro-5-methoxyphenyl)-2-cyano-2-propenamide. The acetonitrile filtrate and washing were combined and concentrated aqueous ammonium hydroxide was added. The resulting acetonitrile mixture was stirred for 1 hour. Water was added and stirring was continued for 1 hour. The solid was collected by filtration, washed with water, ethyl acetate and ether, then dried in vacuo to provide 1.92 g (39%) of 6-bromo-4-[(2,4-dichloro-5-methoxyphenyl)amino]-7-methoxy-3-quinolinecarbonitrile as a yellow solid, mp 256-257° C.; $^1$H NMR (400 MHz, DMSO-d$_6$) δ 3.85 (s, 3H), 4.04 (s, 3H), 7.37 (s, 1H), 7.46 (s, 1H), 7.75 (s, 1H), 8.56(s, 1H), 8.89 (s, 1H), 9.93 (s, 1H); MS (ES) m/z451.9, 454.0 (M+H)+

Analysis for $C_{18}H_{12}BrCl_2N_3O_2$; Calcd: C, 47.71; H, 2.67; N, 9.27. Found: C, 47.41; H, 2.67; N, 9.56.

EXAMPLE 37

4-[(2,4-Dichloro-5-methoxyphenyl)amino]-7-iodo-6-methoxy-3-quinolinecarbonitrile To a suspension of 2-cyano-N-(2,4-dichloro-5-methoxyphenyl)-3-[(3-iodo-4-methoxyphenyl)amino]prop-2-enamide (720 mg, 1.39 mmol) in 40 mL of acetonitrile was added 0.2 mL of methanol. The mixture was heated to reflux and phosphorous oxychloride (1.24 mL, 13.9 mmol) was added dropwise, via syringe. This solution was heated at reflux overnight. After 24 hours, the mixture was cooled in an ice-bath and the solid was collected by filtration, washed with cold acetonitrile (40 mL) and then suspended in tetrahydrofuran (100 mL). To both the acetonitrile filtrate and the tetrahydrofuran suspension were added concentrated ammonium hydroxide (2×50 mL) and the mixtures were stirred for 1 hour. Water (2×800 ml) was added and stirring was continued for 2 hours. The resulting solids were combined, washed with hot water and dried under reduced pressure at ~40° C., overnight, to provide 200 mg (29%) of 4-[(2,4-dichloro-5-methoxyphenyl)amino]-7-iodo-6-methoxy-3-quinolinecarbonitrile, as yellow solid, mp 253-254° C.; $^1$H NMR (400 MHz, DMSO-d$_6$) δ 3.86 (s, 3H), 4.00 (s, 3H), 7.33(s, 1H), 7.74(s, 1H), 7.86 (s, 1H), 8.39 (s, 1H), 8.43 (s, 1H), 9.61 (s, 1H); MS (ES) m/z 500.0, 502.1 (M+H)+

Analysis for $C_{18}H_{12}Cl_2IN_3O_2$—$H_2O$; Theory: C, 41.72; H, 2.72; N, 8.11; Found: C, 41.80; H, 2.52; N, 7.87.

EXAMPLE 38

4-[(2,4-Dichloro-5-methoxyphenyl)amino]-6-ethoxy-7-iodo-3-quinolinecarbonitrile

A suspension of 2-cyano-N-(2,4-dichloro-5-methoxyphenyl)-3-[(4-ethoxy-3-iodophenyl)amino]prop-2-enamide (2.0 g, 3.76 mmol) in 100 mL of toluene was heated to reflux and phosphorous oxychloride (3.5 mL, 37.6 mmol) was added dropwise via syringe. This suspension was heated at reflux for 6 hours and additional phosphorous oxychloride (3.5 mL, 37.6 mmol) was added to slowly give a dark solution. After 72 hours the mixture was cooled to room temperature, the solid was filtered and washed with toluene and ether. The light brown solid was dried under reduced pressure at ~40° C., overnight, to provide 1.47 g (76%) of 4-[(2,4-dichloro-5-methoxyphenyl)amino]-6-ethoxy-7-iodo-3-quinolinecarbonitrile as a yellow solid, mp 213-215° C.; $^1$H NMR (300 MHz, DMSO-d$_6$) δ 1.48 (t, 3H, J=6.9 Hz), 4.32 (q, 2H, J=6.9 Hz), 3.88 (s, 3H), 7.53 (s, 1H), 7.87 (s, 1H), 8.06 (s, 1H), 8.49 (s, 1H), 9.02 (s, 1H), 11.14 (bs, 1H); MS (ES) m/z514.1 (M+H)+

Analysis for $C_{19}H_{14}Cl_2IN_3O_2$-4.0 HCl; Theory: C, 34.58; H, 2.75; N, 6.37; Found: C, 34.79; H, 2.60; N, 6.13.

EXAMPLE 39

4-[(2,4-Dichloro-5-methoxyphenyl)amino]-7-iodo-6-(2-methoxyethoxy)-3-quinolinecarbonitrile A suspension of 2-cyano-N-(2,4-dichloro-5-methoxyphenyl)-3-{[3-iodo-4-(2-methoxyethoxy)phenyl] amino}acrylamide (1.0 g, 1.80 mmol) in 35 mL of toluene was heated to reflux and phosphorous oxychloride (1.7 mL, 18.0 mmol) was added dropwise. The mixture was heated at reflux for 2 hours, and an additional 1.7 mL of phosphorous oxychloride was added. The mixture was continued to heat at reflux for 2 hours, and an additional 1.7 mL of phosphorous oxychloride was added and the reaction mixture was heated at reflux overnight. The reaction is then cooled to room temperature and water was added followed by 10 N sodium hydroxide. The mixture was stirred in an ice-bath for 30 minutes and the precipitate was collected by filtration, washed with methylene chloride to give 870 mg of 4-[(2,4-dichloro-5-methoxyphenyl)amino]-7-iodo-6-(2-methoxyethoxy)-3-quinolinecarbonitrile as a yellow solid; $^1$H NMR (400 MHz, DMSO-d$_6$) δ 3.41 (s, 3H), 3.81 (t, 2H), 3.87 (s, 3H), 4.34 (t, 2H), 7.40 (s, 1H), 7.78 (s, 1H), 7.88 (s, 1H), 8.43 (s, 1H), 8.45 (s, 1H), 9.85 (s, 1H); MS (ES) m/z542.1, 544.1 (M−H)−

Analysis for $C_{20}H_{16}Cl_2IN_3O_3$-4.0 HCl; Calcd: C, 34.81; H, 2.92; N, 6.09. Found: C, 35.04; H, 2.53; N, 5.95.

EXAMPLE 40

7-Bromo-4-[(2,4-dichloro-5-methoxyphenyl)amino]-3-quinolinecarbonitrile

A suspension of 2-cyano-N-(2,4-dichloro-5-methoxyphenyl)-3-[(3-bromo)phenyl)amino]acrylamide (1.5 g, 3.40 mmol) in 50 mL of acetonitrile was heated to reflux and phosphorous oxychloride (4.0 mL, 42.4 mmol) was added dropwise. The mixture was heated at reflux overnight. The reaction was cooled to room temperature and the volatiles were removed in vacuo. Ice was added to the residue followed by saturated aqueous sodium bicarbonate. The mixture was stirred and then extracted with ethyl acetate. The organic layer was washed with water, dried over magnesium sulfate, filtered and concentrated in vacuo. The residue was recrystallized from ethyl acetate to provide 310 mgs of 7-bromo-4-[(2,4-dichloro-5-methoxyphenyl)amino]-3-quinolinecarbonitrile. The mother liquor was concentrated in vacuo and purified by flash column chromatography eluting with a gradient of 3:1 hexane:ethyl acetate to 1:1 hexane:ethyl acetate to give 310 mg of 7-bromo-4-[(2,4-dichloro-5-methoxyphenyl)amino]-3-quinolinecarbonitrile as a light orange solid; $^1$H NMR (400 MHz, TFA/DMSO-$d_6$) δ 3.87 (s, 3H), 7.42 (s, 1H), 7.79 (s, 1H), 7.97 (s, 1H), 8.14 (s, 1H), 8.56 (s, 1H), 8.85 (s, 1H); MS (ES) m/z 422.0, 423.9, 426.0 (M+H)+

Analysis for $C_{17}H_{10}BrCl_2N_3O$; Calcd: C, 48.26; H, 2.38; N, 9.93. Found: C, 48.47; H, 2.37; N, 9.70.

EXAMPLE 41

7-[(2,4-Dichloro-5-methoxyphenyl)amino]thieno[3,2-b]pyridine-6-carbonitrile

A suspension of 2-cyano-N-(2,4-dichloro-5-methoxyphenyl)-3-(thien-3-ylamino)prop-2-enamide (500 mg, 1.35 mmol) in 35 mL of acetonitrile was heated to reflux and phosphorous oxychloride (0.84 mL, 8.98 mmol) was added dropwise. The mixture was heated at reflux overnight. The resultant solution was concentrated in vacuo and the residue was cooled to 0° C. Ice water was added followed by the slow addition of saturated aqueous sodium bicarbonate. The mixture was stirred for 10 minutes then partitioned between ethyl acetate and additional saturated aqueous sodium bicarbonate. The organic layer was washed with water, dried over magnesium sulfate, filtered and concentrated in vacuo. The residue was triturated with ethyl acetate and hexane to provide 337 mg (71%) of 7-[(2,4-dichloro-5-methoxyphenyl)amino]thieno[3,2-b]pyridine-6-carbonitrile, mp 208-210° C.; $^1$H NMR (400 MHz, DMSO-$d_6$) δ 3.85 (s, 3H), 7.39 (s, 1H), 7.46 (d, J=5 Hz, 1H), 7.76 (s, 1H), 8.11 (d, J=5 Hz, 1H), 8.61 (s, 1H), 9.74 (s, 1H); MS (ES) m/z348.1, 350.0 (M–H)–

Analysis for $C_{15}H_9Cl_2N_3O_2S$-0.5 $H_2O$; Calcd: C, 50.15; H, 2.81; N, 11.70. Found: C, 50.32; H, 2.62; N, 11.54.

EXAMPLE 42

1-[3-(2-Methoxy-5-nitro-phenoxy)-propyl]-4-methyl-piperazine

2(3-chloropropoxy)-1-methoxy-4-nitrobenzene, (100 g, 0.407 mol) and sodium iodide (9.2 g, 0.614 mol) was added to 520 mL of dry 1,2-dimethoxyethane. To the mixture was then added N-methylpiperazine (82 g, 0.814 mol). Stirred and heated the reaction to reflux. The reaction was monitored by HPLC. After 8 hours, the heating mantle was removed and the reaction was allowed to cool to ambient temperature. The reaction mixture was then drowned in 1 L of ethyl acetate and stirred for a minimum of 1 hour. Bright yellow solids precipitated. The mixture was filtered and rinsed and the salts collected with ethyl acetate. The filtrate was washed once with 400 mL of 0.5 N NaOH. The layers were separated and the organic layer was washed with water (3×390 mL). The combined organic layers were concentrated under vacuum at 35-40° C. to obtain 97.8 g (light orange oil) (77%); $^1$H NMR (300 MHz, CDCl$_3$) δ 7.91 (dd, J=2.6, 9 Hz, 1H), 7.77 (d, J=2.6 Hz, 1H), 6.90 (d, J=9 Hz, 1H), 4.14 (t, J=7 Hz, 2H), 3.96 (s, 3H) 2.54 (t, J=7 Hz, 2H), 2.48 (m, 8H), 2.30 (s, 3H), 2.06 (m, 2H); MS (ES) m/z310.1 (M+H).

EXAMPLE 43

4-Methoxy-3-[3-(4-methyl-piperazin-1-yl)-propoxy]-phenylamine

To a solution of 1-[3-(2-methoxy-5-nitro-phenoxy)-propyl]-4-methyl-piperazine (2.5 g, 8.1 mmol) in 25 mL of iso-propanol was added 10% Pd-C (0.25 g, 10 wt. %). This mixture was shaken under 35-40 psi of hydrogen in a Parr shaker until hydrogen uptake ceased. The reaction mixture was purged with nitrogen and filtered through celite. The resulting solution was concentrated in vacuo to give the crude 4-methoxy-3-[3-(4-methyl-piperazin-1-yl)-propoxy]-phenylamine as a yellow oil which was used directly in the coupling step described below. $^1$H NMR (300 MHz, CDCl$_3$) δ 6.71 (d, J=8 Hz, 1H), 6.33 (d, J=2.4 Hz, 1H), 6.23 (dd, J=2.4, 8 Hz, 1H), 4.05 (t, J=8 Hz, 2H), 3.80 (s, 3H), 2.53 (m,10H), 2.30 (s, 3H), 2.02 (m, 2H).

EXAMPLE 44

2-Cyano-N-(2,4-dichloro-5-methoxyphenyl)-3-{4-methoxy-3-[3-(4-methylpiperazin-1-yl)-propoxy]-phenylamino}-acrylamide To a suspension of 2-cyano-N-(2,4-dichloro-5-methoxyphenyl)acetamide (1.75 g, 6.75 mmol) in 8.2 mL of iso-propanol was added triethylorthoformate (1.5 g, 10.1 mmol). The mixture was heated to reflux. After 20 minutes, 4-methoxy-3-[3-(4-methyl-piperazin-1-yl)-propoxy]-phenylamine in 20 mLs of iso-propanol was added dropwise so as to maintain reflux. After 26 hours, the reaction was cooled to room temperature and the suspended solids were filtered. The solids were rinsed with iso-propanol until effluent was colorless. The yellow solid was dried in vacuo to give 3.45 g (93%) of 2-cyano-N-(2,4-dichloro-5-methoxyphenyl)-3-{4-methoxy-3-[3-(4-methylpiperazin-1-yl)-propoxy]-phenylamino}-acrylamide as a mixture of isomers. $^1$H NMR (300 MHz, CDCl$_3$) δ 11.35 (br d, 1H), 8.17 (m, 2H), 7.76 (d, 1H), 7.41 (s, 1H), 6.88 (m, 1H) 6.69 (m, 2H), 4.10 (t, J=7 Hz, 2H), 3.96 (s, 3H), 3.87 (s, 3), 2.55 (t, J=7 Hz, 2H), 2.48 (m, 8H), 2.29 (s, 3H), 2.06 (m, 2H); MS (ES) m/z548.1 (M+)

Analysis for $C_{10}H_{14}ClNO_2$; Calcd: C, 55.69; H, 6.54; N, 6.49. Found: C, 55.49; H, 6.59; N, 6.32.

EXAMPLE 45

4-[(2,4-Dichloro-5-methoxyphenyl)amino]-6-methoxy-7-[3-(4-methyl-piperazin-1-yl)-propoxy-3-quinolinecarbonitrile A suspension of 2-cyano-N-(2,4-dichloro-5-methoxyphenyl)-3-{4-methoxy-3-[3-(4-methylpiperazin-1-yl)-propoxy]-phenylamino}-acrylamide (6 g, 10.9 mmol) in 9 mL of acetonitrile was heated to reflux and phosphorous oxychloride (21.8 g, 142 mmol) was added dropwise. The reaction mixture was heated at reflux for 40 hours, then cooled to room temperature. The mixture was cooled to 0° C. and 10N sodium hydroxide was added slowly and carefully to neutralize the reaction. The quench was very exothermic; the addition of sodium hydroxide was such that the temperature of the mixture was kept below 55° C. The mixture was basified to pH 9-10. After cooling to <30° C., 500 mL of ethyl acetate was added and the resulting mixture was stirred for 15 minutes. The solids were filtered and then rinsed with ethyl acetate. The filtrate layers were separated and the organic layer was concentrated in vacuo. The crude oil was dissolved in 45 mL of methanol and stirred at room temperature for 1 hour. The crystalline solid that formed was filtered and rinsed with minimal cold methanol. The filtrate was concentrated and the procedure repeated with about half as much methanol. The two crops were combined to give 4.3 g (75%) of crude 4-[(2,4-dichloro-5-methoxyphenyl)amino]-6-methoxy-7-[3-(4-methyl-piperazin-1-yl)-propoxy-3-quinoline-3-carbonitrile; $^1$H NMR (300 MHz) δ 8.71 (s, 1H), 7.50 (s, 1H), 7.43 (s, 1H), 6.90 (s, 1H), 6.46 (s, 1H), 4.26 (t, J=7 Hz, 2H), 3.78 (s, 3H), 3.67 (s, 3H), 2.57 (t, J=7 Hz, 2H), 2.48 (m, 8H), 2.29 (s, 3H), 2.12 (m, 2H); MS (ES) m/z265.6, 530.1 (M+)

EXAMPLE 46

4-(2-Methoxy-5-nitrophenyl)-2-furaldehyde

To a mixture of 2-iodo-4-nitroanisole (565 mg, 2.02 mmol) and 2-formylfuran-4-boronic acid pinacol ester (670 mg, 3.03 mmol) in 20 mL of ethylene glycol dimethyl ether and 12 mL of aqueous saturated sodium bicarbonate was added 80 mg of tetrakis(triphenylphosphine)palladium (0). The reaction mixture was heated at reflux overnight then allowed to cool to room temperature and added to a biphasic mixture of 10% methanol in ethyl acetate and water. The solid was collected by filtration, washed with ethyl acetate and water to provide 259 mg (52%) of 4-(2-methoxy-5-nitrophenyl)-2-furaldehyde as a light brown solid, 1H NMR (DMSO-d6) d 4.07 (s, 3H), 7.37 (d, J=9 Hz, 1H), 1H), 8.20-8.29 (m, 2H), 8.55 (d, J=3 Hz, 1H), 8.69 (s, 1H), 9.68 (s, 1H); MS 247.1 (M−H)−.

EXAMPLE 47

1-{[4-(2-Methoxy-5-nitrophenyl)-2-furyl]methyl}-4-methylpiperazine

A mixture of 4-(2-methoxy-5-nitrophenyl)-2-furaldehyde (230 mg, 0.93 mmol) and N-methylpiperazine (0.90 mL, 8.1 mmol) in 20 mL of dichloromethane and 2 mL of 1-methylpyrolidinone was cooled to 0° C. Sodium triacetoxyborohydride (1.21 g, 5.7 mmol) was added in portions followed by a few drops of acetic acid. The resulting mixture was stirred at 0° C. for 10 minutes then at room temperature for 1.5 hours. The mixture was partitioned between ethyl acetate and saturated aqueous sodium bicarbonate. The organic phase was dried over magnesium sulfate, filtered and concentrated in vacuo. The residue was purified by flash column chromatography eluting with a gradient of 20% methanol in ethyl acetate to 1% ammonium hydroxide in 20% methanol in ethyl acetate. Trituration with diethyl ether and hexane provided 57 mg (18%) of 1-{[4-(2-methoxy-5-nitrophenyl)-2-furyl]methyl}-4-methylpiperazine as a light yellow solid, $^1$H NMR (DMSO-d$_6$) δ 2.14 (s, 3H), 2.25-2.36 (broad s, 4H), 2.38-2.46 (broad s, 4H), 3.52 (s, 2H), 4.04 (s, 3H), 6.96 (s, 1H), 7.31 (d, J=8 Hz, 1H), 8.14-8.20 (m, 2H), 8.38 (d, J=3 Hz, 1H); MS 332.1 (M+H)+.

Analysis for $C_{17}H_{21}N_3O_4$: Calcd: C, 61.62; H, 6.39; N, 12.68. Found: C, 61.46; H, 6.68; N, 12.54.

EXAMPLE 48

(4-Methoxy-3-{5-[(4-methylpiperazin-1-yl)methyl]-3-furyl}phenyl)amine

To a solution of 1-{[4-(2-methoxy-5-nitrophenyl)-2-furyl]methyl}-4-methylpiperazine (396 mg, 1.19 mmol) in 20 mL of methanol was added 10% palladium on carbon (40 mg). The resulting mixture was shaken with hydrogen in a Parr shaker until hydrogen uptake ceased. The reaction mixture was filtered through Celite and the filtrate concentrated in vacuo to give 358 mg (100%) of (4-methoxy-3-[5-[(4-methylpiperazin-1-yl)methyl]-3-furyl}phenyl)amine as a brown oil, $^1$H NMR (DMSO-d$_6$) δ 2.14 (s, 3H), 2.29 (broad s, 4H), 2.40 (broad s, 4H), 3.49 (s, 2H), 3.72 (s, 3H), 4.61 (s, 2H), 6.47 (d, J=8 Hz, 1H), 6.58 (s, 1H), 6.78 (d, J=9 Hz, 1H), 6.80 (s, 1H), 7.91 (s, 1H); MS 302.1 (M+H)+.

ALTERNATIVE EXAMPLE 48

(4-Methoxy-3-{5-[(4-methylpiperazin-1-yl)methyl]-3-furyl}phenyl)amine

To a solution of 1-[(4-bromo-2-furyl)methyl]-4-methylpiperazine (1.43 g, 5.52 mmol) and tri-isopropyl borate (1.76 g, 9.38 mmol) in 20 mL of tetrahydrofuran at −78° C. was added 1.6 M n-butyl lithium in hexane (5.38 mL, 8.61 mmol) over 10 minutes. After stirring at −78° C. for 10 minutes, the temperature of the reaction mixture was allowed to rise to room temperature. Water (1.0 mL) was added and the solvents were removed in vacuo. The resultant intermediate boronic acid was dissolved in 20 mL of ethylene glycol dimethyl ether and 2-iodo-4-nitroanisole (1.06 mg, 4.25 mmol) and [1,1'-bis(diphenylphosphino)ferrocene]dichloropalladium(II), complex with dichloromethane (1:1) (87 mg, 0.11 mol) were added. A solution of 2.25 g of sodium carbonate in 6.5 mL of water was added and the resulting mixture was heated at reflux for 3 hours. The mixture was cooled to room temperature and partitioned between ethyl acetate and water. The aqueous layer was further extracted with ethyl acetate and the organic layers were combined, washed with brine, dried over sodium sulfate, filtered and concentrated in vacuo. The residue was purified by flash column chromatography, eluting with a gradient of 5% methanol in dichloromethane to 10% methanol in dichloromethane to give 900 mg (70%) of (4-methoxy-3-{5-[(4-methylpiperazin-1-yl)methyl]-3-furyl}phenyl)amine as a red oil.

EXAMPLE 49

2E/Z)-2-Cyano-N-(2,4-dichloro-5-methoxyphenyl)-3-[(4-methoxy-3-{5-[(4-methylpiperazin-1-yl)methyl]-3-furyl}phenyl)amino]acrylamide To a suspension of 2-cyano-N-(2,4-dichloro-5-methoxyphenyl)acetamide (261 mg, 1.01 mmol) in 5 mL of iso-propanol was added triethylorthoformate (0.504 mL, 3.03 mmol). The mixture was heated to reflux and (4-methoxy-3-{5-[(4-methylpiperazin-1-yl)methyl]-3-furyl}phenyl)amine (320 mg, 1.06 mmol) in 9 mL of iso-propanol was added dropwise. This mixture was heated at reflux for 25 hours. The mixture was allowed to cool to room temperature and the solid was collected by filtration, washed with iso-propanol, to provide 465 mg (81%) of (2E/Z)-2-cyano-N-(2,4-dichloro-5-methoxyphenyl)-3-[(4-methoxy-3-{5-[(4-methylpiperazin-1-yl)methyl]-3-furyl}phenyl)amino]acrylamide as a gray solid, mp 198-199° C.; MS 570.1 (M+H)+.

Analysis for $C_{28}H_{29}Cl_2N_5O_4$-0.2 $H_2O$: Calcd: C, 58.58; H, 5.16; N, 12.20. Found: C, 58.50; H, 5.07; N, 12.07.

EXAMPLE 50

4-[(2,4-Dichloro-5-methoxyphenyl)amino]-6-methoxy-{7-[5-[(4-methylpiperazin-1-yl)methyl]-3-furyl}-3-quinolinecarbonitrile A suspension of (2E/Z)-2-cyano-N-(2,4-dichloro-5-methoxyphenyl)-3-[(4-methoxy-3-{5-[(4-methylpiperazin-1-yl)methyl]-3-furyl}phenyl)amino]acrylamide (409 mg, 0.72 mmol) in 20 mL of butyronitrile was heated to 105° C. and phosphorous oxychloride (0.856 mL, 9.36 mmol) was added dropwise. After 14 hours additional phosphorous oxychloride (0.430 mL) was added, and the reaction mixture was heated at 105° C. for an additional 8 hours. Additional phosphorous oxychloride (0.430 mL) was added and the reaction temperature was increased to 115° C. The reaction mixture was heated at 115° C. for 18 hours. Additional phosphorous oxychloride (0.856 mL) was added and the reaction mixture was heated at 115° C. for an additional 26 hours. The reaction mixture was concentrated in vacuo and the residue suspended in a 1:1 mixture of ethyl acetate and tetrahydrofuran and neutralized with concentrated ammonium hydroxide. The mixture was stirred at room temperature for 1 hour. The solvents were removed in vacuo and the residue was purified by flash column chromatography eluting with a gradient of dichloromethane to 20% methanol in dichloromethane. Subsequent preparative thin layer chromatography developing with 10% methanol in dichloromethane gives 61 mg (15%) of 4-[(2,4-dichloro-5-methoxyphenyl)amino]-6-methoxy-{7-[5-[(4-methylpiperazin-1-yl)methyl]-3-furyl}-3-quinolinecarbonitrile as a yellow solid, mp 174-176° C.

Calc'd: 552.15638; Found: 552.15723. HPLC: 96.8%.

What is claimed is:

1. A process for the preparation of a 4-amino-3-quinolinecarbonitrile comprising:
   a. combining an amine compound with cyanoacetic acid and an acid catalyst to yield a cyanoacetamide;
   b. condensing the cyanoacetamide of step a with an aniline, an alcoholic solvent, and a trialkylorthoformate to yield 3-amino-2-cyanoacrylamide; and
   c. combining the 3-amino-2-cyanoacrylamide with phosphorus oxychloride in acetonitrile, butyronitrile, toluene or xylene, optionally in the presence of a catalyst to yield a 4-amino-3-quinolinecarbonitrile.

2. The process of claim 1 wherein the ratio of cyanoacetic acid to amine is 1 to 1.5 equivalents.

3. The process of claim 1 wherein the ratio of cyanoacetic acid to amine is 1.03 equivalents.

4. The process of claim 1 wherein the aniline is a hydrochloride salt.

5. The process of claim 1 wherein the aniline is a free base.

6. The process of claim 1 wherein the alcoholic solvent is iso-propanol.

7. The process of claim 1 wherein the condensing step occurs at a temperature of 10-200° C.

8. The process of claim 1 wherein the condensing step occurs at a temperature of 20-140° C.

9. The process of claim 1 wherein the condensing step occurs at a temperature of 80° C.

10. The process of claim 1 wherein the catalyst is an alcohol.

11. The process of claim 1 wherein the catalyst is an amine base.

12. The process of claim 1 wherein the combining of step c occurs at a temperature of 50-200° C.

13. The process of claim 1 wherein the combining of step c occurs at a temperature of 80-110° C.

* * * * *